US012642692B2

(12) United States Patent
Harsy

(10) Patent No.: US 12,642,692 B2
(45) Date of Patent: Jun. 2, 2026

(54) COLD THERAPY DEVICE AND METHOD

(71) Applicant: Douglas R. Harsy, Southlake, TX (US)

(72) Inventor: Douglas R. Harsy, Southlake, TX (US)

(73) Assignee: CryoDynamics, Inc., Southlake, TX (US)

( * ) Notice: Subject to any disclaimer, the term of this patent is extended or adjusted under 35 U.S.C. 154(b) by 486 days.

(21) Appl. No.: 18/119,426

(22) Filed: Mar. 9, 2023

(65) Prior Publication Data

US 2024/0299210 A1 Sep. 12, 2024

Related U.S. Application Data

(63) Continuation-in-part of application No. 16/898,543, filed on Jun. 11, 2020, now Pat. No. 11,793,670.

(51) Int. Cl.
*A61F 7/00* (2006.01)

(52) U.S. Cl.
CPC .... *A61F 7/0085* (2013.01); *A61F 2007/0056* (2013.01)

(58) Field of Classification Search
CPC ...................... A61F 7/0085; A61F 2007/0056
See application file for complete search history.

(56) References Cited

U.S. PATENT DOCUMENTS

| | | | | |
|---|---|---|---|---|
| 7,204,041 B1 * | 4/2007 | Bailey, Sr. | ........... | A43B 13/203 |
| | | | | 36/1 |
| 9,566,187 B2 * | 2/2017 | Edelman | ................... | A61F 7/10 |
| 2011/0238051 A1 * | 9/2011 | Levinson | ................. | A61F 7/02 |
| | | | | 606/22 |
| 2014/0350648 A1 * | 11/2014 | Ericson | ................. | A61M 39/24 |
| | | | | 607/105 |
| 2016/0354140 A1 * | 12/2016 | Sharma | ................. | A61B 90/39 |

* cited by examiner

*Primary Examiner* — Joanne M Rodden
*Assistant Examiner* — Dana Stumpfoll
(74) *Attorney, Agent, or Firm* — D. Tiller Law PLLC; Don Tiller

(57) ABSTRACT

A cold therapy apparatus includes a thermal body wrap with umbilical to a control unit with pump for circulating a thermal fluid to remove heat from a body. A coolant heat exchange assembly includes a thermal fluid reservoir and a coolant tank that has a heat exchanger inside, immersed in the coolant. The heat exchanger is coupled to the control unit to circulate the thermal fluid through the thermal body wrap. The coolant heat exchange assembly is removed from the control unit and placed in a cold environment to chill the coolant, and is then re-coupled during cold therapy.

15 Claims, 19 Drawing Sheets

Section A-A
Exploded

80

Section B-B
Exploded

80

Section A-A

Section B-B

190

247

Section C-C

Section D-D

500

COLD THERAPY DEVICE AND METHOD

RELATED APPLICATIONS

The present application is a continuation-in-part of U.S. patent application Ser. No. 16/898,543 filed on Jun. 11, 2020.

BACKGROUND OF THE INVENTION

Field of the Invention

The present invention relates to cold therapy devices. More particularly, the present disclosure relates to a cold therapy apparatus that employs a removable coolant heat exchange unit, which can be placed in a cold environment for a period of time to remove heat from its coolant to reduce its temperature, and which can be re-coupled with the cold therapy apparatus to serve as its thermal reserve during cold therapy.

Background of the Invention

The benefits of cold therapy in treatment of various human and animal conditions are well documented. Various apparatuses have been devised to achieve the desired transfer of heat between a creature, human or animal, and such an apparatus. A classic examples is the ice pack. Modern medicine now recommends specific amounts of heat transfer for specific durations of time as are indicated for various physical ailments and conditions. For example, soft tissue injuries often indicate cold therapy immediately after injury for a recommended period of time.

Traditionally, cold therapy has been accomplished with the affected individual in a fixed position. Such thinking corresponded to the concept of limited physical movement of the patient during cold therapy or recovery from injury. However, patients often desire some degree of mobility during therapy. Movement and mobility during cold therapy, generally thermal therapy, is acceptable in the case where there is no undue strain to the affected portion of the patient's body. In fact, some movement of the affected area is tolerable, and sometimes even desirable. Given the need and desire for mobility during thermal therapy, some devices and apparatus have been brought to market. One example is the ice chest and bladder cold therapy system. In the ice chest system, the user carries an insulated chest that contains a mixture of ice and water, along with a pump and battery. A pair of hoses is coupled between the chest and pump, and to a thermal body wrap, which is held against the affected portion of the patient's body. The patient is able to carry the chest as they move about. Such systems are cost effective, but some significant limitations to this approach are the size and bulk of the systems for carrying about, and the cold temperature available with ice water. Thermoelectric cooling systems are also know, which force heat transfer by the Peltier Effect, however such system are not generally cost effective in practice.

In the case of a cold therapy apparatus that relies upon a chilled substance, many of the prior art devices employ a reserve of water and ice, where the water portion is circulated through the thermal body wrap. As is well understood, that water portion of an ice water mixture will be near 32° Fahrenheit, which carries a risk of excessive temperature drop in the affect area of the body being treated. This type of system also requires a substantial bulk, the need to replenish the ice supply, and the requirement to disposed water resulting from the melted ice. Thus it can be appreciated that there is a need in the art for a cold therapy apparatus and method to address the problems in the prior art.

SUMMARY OF THE INVENTION

The need in the art is addressed by the apparatuses and methods of the present invention. The present disclosure teaches a cold therapy apparatus for removing heat from a body, such as a human body. The apparatus includes a thermal body wrap that is coupled through an umbilical tube assembly to a control unit, for circulating a thermal fluid to remove heat from a body with which the thermal body wrap may be engaged. The control unit includes a pump that is fluidly coupled to circulate the thermal fluid from a supply coupler, through the umbilical tube assembly and the thermal body wrap, to a return coupler. A coolant heat exchange assembly includes a coolant tank that is filled with a coolant and has a heat exchanger inside that is immersed in the coolant. The heat exchanger fluidly couples to a thermal fluid inlet coupler and a thermal fluid outlet coupler, both present an exterior surface of the coolant tank, to circulate the thermal fluid through it, and thereby transfer heat from the thermal fluid to the coolant. The supply coupler and the return coupler are removably engaged with the thermal fluid inlet coupler and the thermal fluid outlet coupler, respectively, to enable the thermal fluid to circulate between the heat exchanger and the thermal body wrap, while enabling separation of the coolant heat exchange assembly from the control unit such that the coolant heat exchange assembly may be intermittently located in a cold environment to remove heat from the coolant.

In a specific embodiment, the foregoing apparatus further includes an insulated enclosure with an opening for receiving the coolant heat exchange assembly while it is engaged with the control unit, to thereby substantially insulate the coolant heat exchange assembly against the coupling of external heat thereinto. In a refinement to this embodiment, a portion of the insulated enclosure is fixed to the coolant heat exchange assembly and is configured such that the opening is substantially closed by the portion when the coolant heat exchange assembly is inserted into the insulated enclosure.

In a specific embodiment of the foregoing apparatus, the heat exchanger includes an inlet manifold that is fluidly coupled to an outlet manifold through plural heat exchange tubes, and, the inlet manifold is fluidly coupled to the thermal fluid inlet coupler, and the outlet manifold is fluidly coupled to the thermal fluid outlet coupler.

In a specific embodiment of the foregoing apparatus, the coolant tank includes a first coolant tank portion and a second coolant tank portion, which are located on opposing sides of the heat exchanger, and contain a first portion of the coolant and a second portion of the coolant, respectively, such that the heat exchanger is thermally exposed on opposing sides thereof to both of the first coolant portion and the second coolant portion.

In a specific embodiment of the foregoing apparatus, the thermal fluid inlet coupler and the thermal fluid outlet coupler are coupled through at least one of the first coolant tank portion and the second coolant tank portion.

In specific embodiment of the foregoing apparatus, the first coolant tank portion and the second coolant tank portion are partially enclosed by a first coolant tank cover and a second coolant tank cover, respectively. In a refinement to this embodiment, the thermal fluid inlet coupler and the thermal fluid outlet coupler are coupled through at least one of the first coolant tank cover and the second coolant tank cover.

In a specific embodiment of the foregoing apparatus, the first coolant tank cover and the first coolant tank portion, and second coolant tank cover and the second coolant tank portion, are formed of a thermoplastic material having spring clips and cooperatively aligned lugs, monolithically molded therewith, and disposed therebetween, to facilitate assembly by spring-snap action.

In a specific embodiment of the foregoing apparatus, the heat exchanger includes a first heat exchanger portion and a second heat exchanger portion, which are joined together in clamshell fashion to define plural heat exchange tubes fluidly coupled with an inlet manifold and an outlet manifold. In a refinement to this embodiment, the first heat exchanger portion and the second heat exchanger portion are join together with mechanical fasteners, and have a seal disposed therebetween. In another refinement to this embodiment, the first heat exchanger portion and the second heat exchanger portion are formed of a thermoplastic material having spring clips and cooperatively aligned lugs, monolithically molded therewith, and disposed therebetween, to facilitate assembly by spring-snap action.

In a specific embodiment of the foregoing apparatus, the first coolant tank portion and the first heat exchanger portion are formed together as a unit, and the second coolant tank portion and the second heat exchanger portion are formed together as a unit. In a refinement to this embodiment, the first coolant tank portion and the first heat exchanger portion unit, and the second coolant tank portion and the second heat exchanger portion unit are formed from thermoplastic.

In a specific embodiment of the foregoing apparatus, the first coolant tank portion and the first heat exchanger portion unit, and the second coolant tank portion and the second heat exchanger portion unit are formed of a thermoplastic material having spring clips and cooperatively aligned lugs, monolithically molded therewith, and disposed therebetween, to facilitate assembly by spring-snap action.

In a specific embodiment of the foregoing apparatus, the coolant is water mixed with an additive to prevent freezing above a temperature of minus twenty-fide degrees Fahrenheit, and the thermal fluid is selected from a mixture of water and isopropyl alcohol or propylene glycol, which mixture prevents freezing above a temperature of minus twenty-fide degrees Fahrenheit.

In a specific embodiment of the foregoing apparatus, the supply coupler, the return coupler, the thermal fluid inlet coupler and the thermal fluid outlet coupler are quick-connect tubing couplers with automatic shut-off valves to prevent the thermal fluid from leaking when disconnected.

In a specific embodiment of the foregoing apparatus, the heat exchanger is fabricate from high density polyethylene (HDPE) plastic.

The present disclosure teaches a method for removing heat from a body using a cold therapy apparatus, which includes a control unit with a pump that is fluidly coupled from a supply coupler on the control unit, through an umbilical tube assembly and a thermal body wrap, to a return coupler on the control unit, where the apparatus further includes a coolant heat exchange assembly that has a coolant tank with a heat exchanger inside that is fluidly coupled to a thermal fluid inlet coupler and a thermal fluid outlet coupler, and both disposed on the exterior of the coolant tank. The method includes the steps of filing the coolant tank with a coolant, which immerses the heat exchanger in the coolant, and then placing the coolant heat exchange assembly in a cold environment, to remove heat from the coolant that is in the coolant tank, and then, removing the coolant tank assembly from the cold environment. The method also includes coupling the control unit supply coupler and return coupler with the heat exchange assembly thermal fluid outlet coupler and the thermal fluid inlet coupler, respectively, and, filling the heat exchanger, pump, umbilical tube assembly, and thermal body wrap with a thermal fluid. And, engaging the thermal body wrap with a body from which heat is to be removed, and operating the pump, thereby circulating the thermal fluid between the thermal body wrap and the heat exchanger, passing through the pump, the umbilical tube assembly, the supply coupler, the return coupler, the thermal fluid inlet coupler and the thermal fluid outlet coupler, and thereby enabling the thermal fluid to transfer heat from the body to the coolant.

In a specific embodiment, the foregoing method further includes placing the the coolant heat exchange assembly into an insulated enclosure, which has an opening for receiving the coolant heat exchange assembly, while engaged with the control unit, thereby substantially insulating the coolant heat exchange assembly against the coupling of external heat thereinto.

In a specific embodiment of the foregoing method, the heat exchanger includes an inlet manifold fluidly coupled to an outlet manifold through plural heat exchange tubes, and the inlet manifold is fluidly coupled to the thermal fluid inlet coupler, and the outlet manifold is fluidly coupled to the thermal fluid outlet coupler.

In a specific embodiment of the foregoing method, the coolant tank includes a first coolant tank portion and a second coolant tank portion, which are located on opposing sides of the heat exchanger, and contain a first portion of the coolant and a second portion of the coolant, respectively, thereby thermally exposing the heat exchanger on opposing sides thereof to both of the first coolant portion and the second coolant portion.

In a specific embodiment of the foregoing method, the heat exchanger includes a first heat exchanger portion and a second heat exchanger portion, which are joined together in clamshell fashion to define plural heat exchange tubes fluidly coupled with an inlet manifold and an outlet manifold.

In a specific embodiment of the foregoing method, the first coolant tank portion and the first heat exchanger portion are formed together as a unit, and the second coolant tank portion and the second heat exchanger portion are formed together as a unit.

In a specific embodiment of the foregoing method, the first coolant tank portion and the first heat exchanger portion unit, and the second coolant tank portion and the second heat exchanger portion unit are formed from thermoplastic.

In a specific embodiment of the foregoing method, the coolant is water mixed with a additive to prevent freezing above a temperature of minus twenty-fide degrees Fahrenheit, and, the thermal fluid is selected from a mixture of water and isopropyl alcohol or propylene glycol, which mixture prevents freezing above a temperature of minus twenty-fide degrees Fahrenheit.

In a specific embodiment of the foregoing method, the supply coupler, the return coupler, the thermal fluid inlet coupler and the thermal fluid outlet coupler are quick-connect tubing couplers having automatic shut-off valves therein to prevent the thermal fluid from leaking when disconnected.

DESCRIPTION OF THE INVENTION

Figures 1, 2A, 2B:
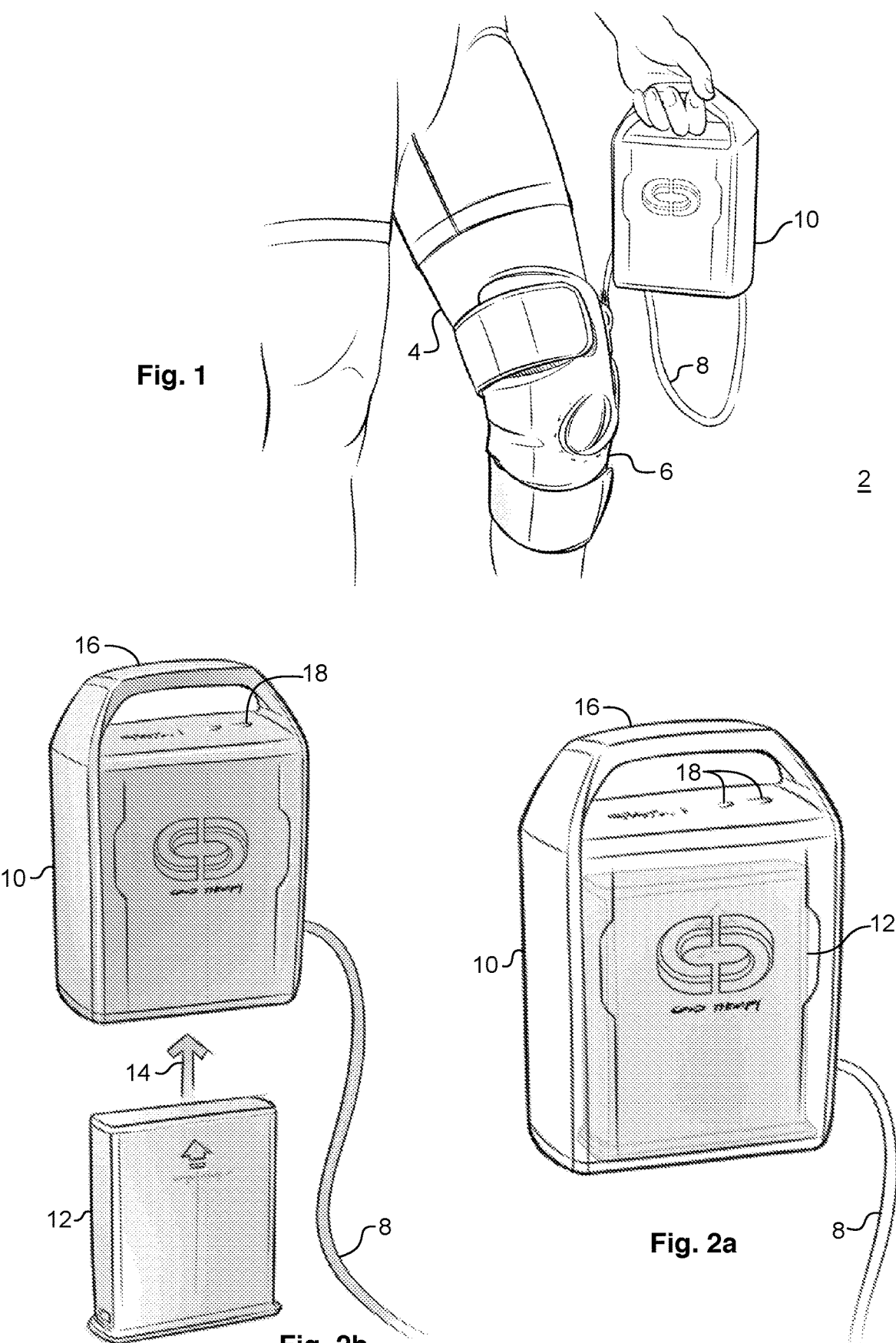
FIG. 1 is a cold therapy apparatus application drawing according to an illustrative embodiment of the present invention.
FIGS. 2*a* and 2*b* are drawing of a cold therapy apparatus drawings according to an illustrative embodiment of the present invention.

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope hereof, and additional fields in which the present invention would be of significant utility.

In considering the detailed embodiments of the present invention, it will be observed that the present invention resides primarily in combinations of steps to accomplish various methods or components to form various apparatus and systems. Accordingly, the apparatus and system components, and method steps, have been represented where appropriate by conventional symbols in the drawings, showing only those specific details that are pertinent to understanding the present teachings so as not to obscure the disclosure with details that will be readily apparent to those of ordinary skill in the art having the benefit of the disclosures contained herein.

In this disclosure, relational terms such as first and second, top and bottom, upper and lower, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises a" does not, without more constraints, preclude the existence of additional identical elements in the process, method, article, or apparatus that comprises the element.

Under the cold therapy teachings of the present disclosure, a thermal reserve is provided in the form of a coolant that is contained in a coolant tank, and, that coolant tank has a heat exchanger located inside, which is immersed in the coolant. A thermal fluid is circulated through the heat exchanger, to transfer heat from the thermal fluid and into the coolant. As such, the temperature of the thermal fluid is reduced as it passes through the heat exchanger, and is then pumped to a thermal body wrap, where heat from the body is transferred to the thermal fluid, increasing its temperature, and which is then returned to the heat exchanger. Thus, the thermal reserve, the coolant, is a separate substance from the thermal fluid, which is pumped through a thermal fluid circuit that includes the thermal body wrap. A virtue of this arrangement is that the coolant and the thermal fluid can be different materials with different thermodynamic characteristics. Another virtue of this design is that the coolant and coolant tank can be removed from the overall apparatus, chilled, and reused, without the need or mess associated with disposing of, or replacing, the working fluids.

Reference is directed to FIG. 1, which is a cold therapy apparatus 2 application drawing according to an illustrative embodiment of the present invention. An individual 4 with a knee injury has a thermal body wrap 6 fastened thereabout. The thermal body wrap 6 is fluidly coupled by an umbilical tube assembly 8 to a cold therapy apparatus 10. The cold therapy apparatus 10 is of compact proportions and is suitable for portable operation, including carrying in the hand of the individual 4.

Reference is directed to FIGS. 2a and 2b, which are drawing of a cold therapy apparatus according to an illustrative embodiment of the present invention. The cold therapy apparatus 10 includes a user interface 18 with power and operational controls, and a carrying handle 16 formed integrally therewith. The cold therapy apparatus 10 is thermally insulated and receives 14 a coolant heat exchange assembly 12 therein, which is thereby insulated from external heat sources. An umbilical tube assembly 8 couples the coolant heat exchange assembly 12 to a thermal body wrap (not shown). A benefit of this arrangement is that the coolant heat exchange assembly 12, when removed from the apparatus 10, can be placed in a freezer, or other cold environment, to remove heat therefrom, to thereby "recharge" the unit for continued operation. And, the user may be provided with more than one coolant heat exchange assembly 12 so that their use may be rotated in sequence, to provide continued thermal therapy.

Figure 3:
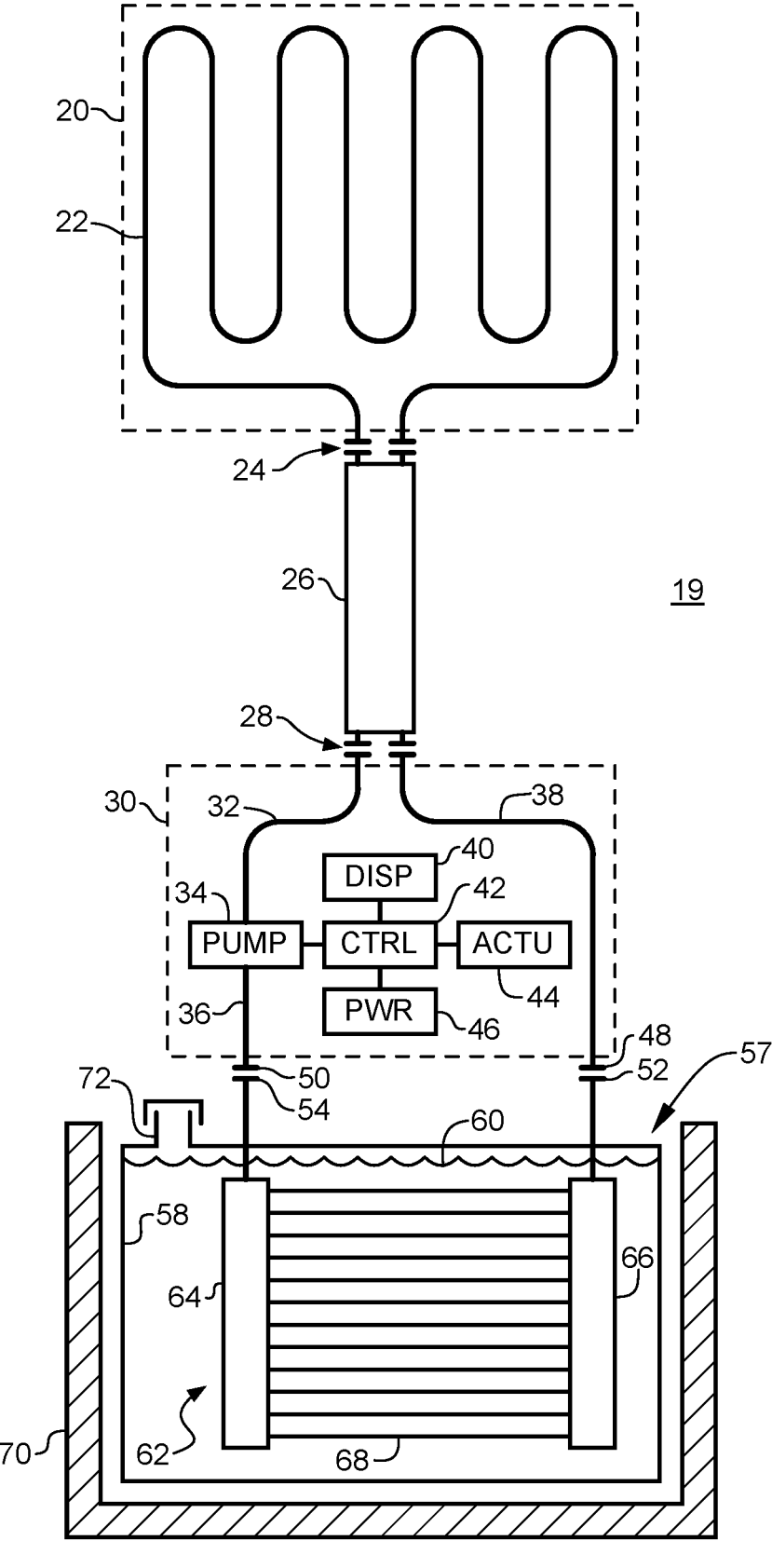
FIG. 3 is a functional block diagram of a cold therapy apparatus according to an illustrative embodiment of the present invention.

Reference is directed to FIG. 3, which is a functional block diagram of a cold therapy apparatus 19 according to an illustrative embodiment of the present invention. A thermal body wrap 20 is coupled through an umbilical tube assembly 26 to a control unit 30, which is, in turn, coupled to a coolant heat exchange assembly 57, which is located within an insulated enclosure 70. The thermal body wrap 20 may take several forms, as are known to those skilled in the art. These may be shaped to fit particular body parts, or may employ a generic configuration. Within the thermal body wrap 20 is a circuitous fluid path 22, through which a working thermal transfer fluid is circulated. Hereinafter referred to a "thermal fluid." The umbilical tube assembly 26 comprises a pair of flexible tubes within an insulated sheath, and is coupled to the thermal body wrap by a first pair of couplers 24, or by permanent connection. The thermal fluid is circulated through the umbilical tube assembly 26 to and from the thermal body wrap 20.

The control unit 30 in FIG. 3 is coupled to the umbilical tube assembly 26 by a second pair of couplers 28, or by permanent connection. The couplers 24, 28 may be selected from a variety of tubing couplers known to those skilled in the art, and quick-couplers are a good choice for convenience. Couplers 24, 28 with built-in shut off valves are useful in preventing thermal fluid leakage when disconnected. Within the control unit are located plural fluid and electrical circuits, which are presented in function block diagram form in FIG. 3. A pump 34 is coupled between tubes 32, 36, which serves as the motive force for circulating the thermal fluid in the cold therapy apparatus 19. Tube 32 is coupled 28 to the umbilical tube assembly 26, and tube 36 is terminated at a thermal fluid inlet coupler 50. The pump 24 may be any of the type known to those skilled in the art, with centrifugal and diaphragm pumps suitable for 12 Vdc nominal operation being good options. The other half of the fluid circuit is tube 38 which couples coupler 28 to the umbilical tube assembly 26 and a thermal fluid outlet coupler 48 on the control unit 30. The tubes 32, 36, 38 may be rigid or flexible, fabricated from metals or polymers. In the illustrative embodiment, flexible ³⁄₁₆" diameter polymeric tubing suitable for use with the thermal fluid is employed. The thermal fluid in the illustrative embodiment is a mixture of water and isopropyl alcohol the prevents freezing at temperatures above –25° F. Other additives and fluids may be utilized.

The electrical circuit functions in FIG. 3 include the aforementioned pump 34, which is connected to a control circuit 42 for providing power thereto at selected times and for selected periods of time. A typical run time is for thirty minutes, however this may be adjusted to suit therapeutic requirements. An actuator 44 is connected to the control circuit 42 for initiating, adjusting, and terminating operation of the pump 34 and other circuit functions. A simple on/off switch may be employed, or a more advanced timing circuit, or microprocessor controlled circuit, depending on the sophistication of system control that may be desired. A power source 46, or power supply interface, is employed for providing electrical power to pump 34 and related circuitry. In the illustrative embodiment, 12 Vdc nominal power is employed, either by battery source or mains powered transformer operation. In addition, a user interface display 40 may be provided to indicate status of operation of the cold therapy apparatus 19. In the illustrative embodiment, a pump-on indicator light is provided, and a count-down timer by sequential illumination of LEDs is employed. A digital display may also be provided.

The thermal fluid supply coupler 50 and return coupler 52 of the control assembly 30 are selectively engaged with corresponding thermal fluid outlet coupler 54 and thermal fluid inlet coupler 52, respectively, in a coolant heat exchange assembly 57. Quick couplers with internal shut-off valves are a suitable choice, but other couplers known to those skilled in the art may also be employed. The coolant heat exchange assembly 57 includes a coolant tank 58, which is filled with a liquid coolant 60 through a coolant fill port 72. The coolant 60 in the illustrative embodiment is a water-based mixture that prevents freezing at temperatures above –25° F., which includes water and a suitable additive. Another illustrative embodiment provides an instant cold pack system that consists of a suitable amount of ammonium nitrate, calcium ammonium nitrate or urea inside that coolant tank, to which water is added to fill the tank. When this occurs, the material dissolves and an endothermic reaction occurs, which quickly absorbs heat from the surroundings, and quickly lowers the coolant temperature. In another embodiment, the apparatus is provided to the end user with the coolant 60 additive and water mixture already filled into the coolant tank 58. Within the coolant tank 58 is heat exchanger 62, immersed in the coolant 60, and coupled to the thermal fluid outlet coupler 54 and thermal fluid inlet coupler 52 such that thermal fluid is circulated through the heat exchanger 62 to transfer heat into the coolant 60.

In the illustrative embodiment of FIG. 3, the heat exchange assembly 62 consists of an inlet manifold 66 coupled though plural heat exchange tubes 68 to and outlet manifold 64. The inlet manifold 66 is fluidly coupled to the thermal fluid inlet coupler 52, and the outlet manifold 64 is fluidly coupled to thermal fluid outlet coupler 54, thereby completing the fluid circuit through the heat exchange assembly 62. In the illustrative embodiment, the coolant heat exchange assembly 57 of the thermal cooling apparatus 19 is positioned within an insulated enclosure 70 while engaged with the cold therapy apparatus 19 to reduce unwanted heat transfer into the coolant, thereby extending available thermal reserve for therapy purposes.

Figure 4:
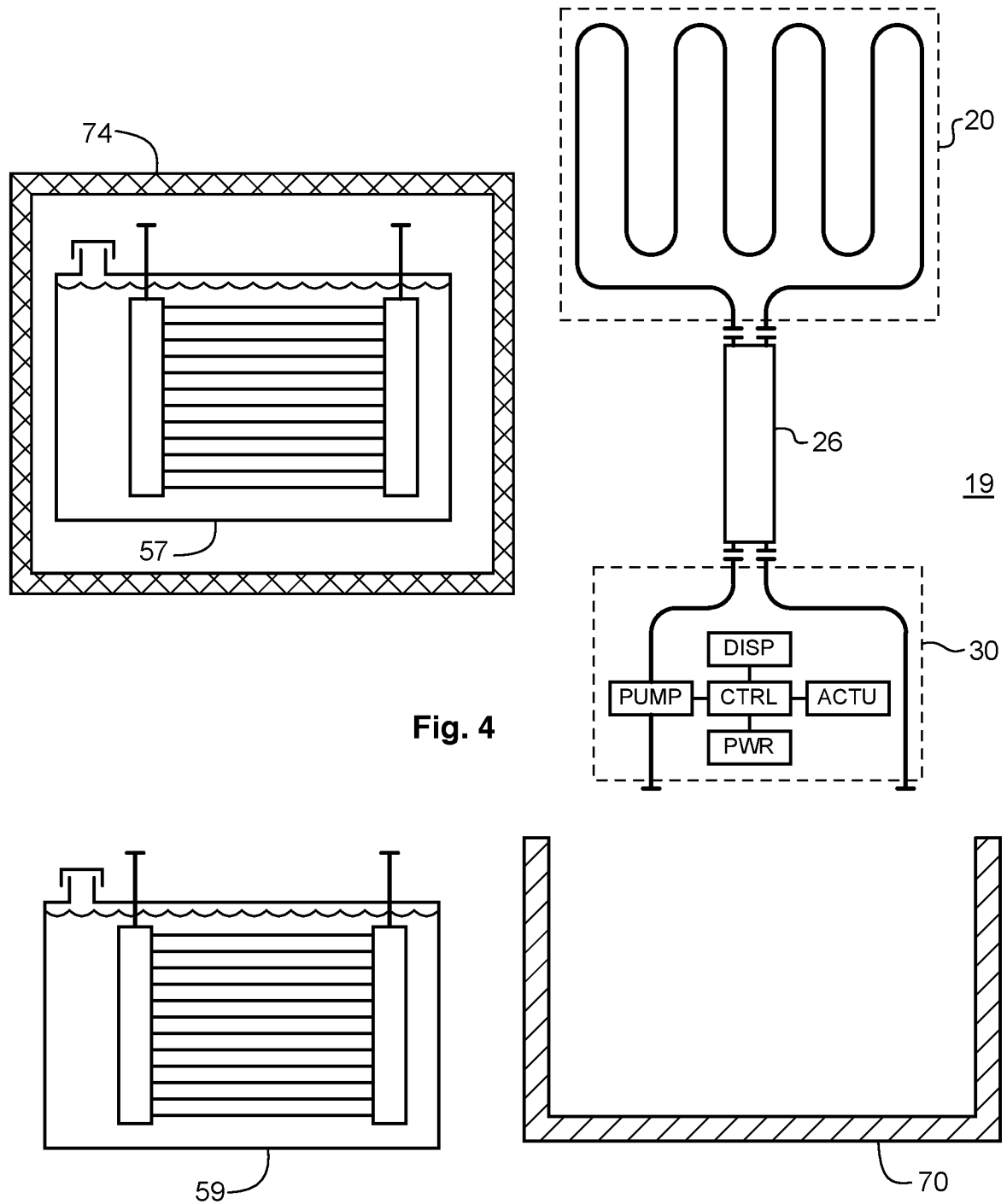
FIG. 4 is a functional block diagram of a cold therapy system according to an illustrative embodiment of the present invention.
Figure 5:
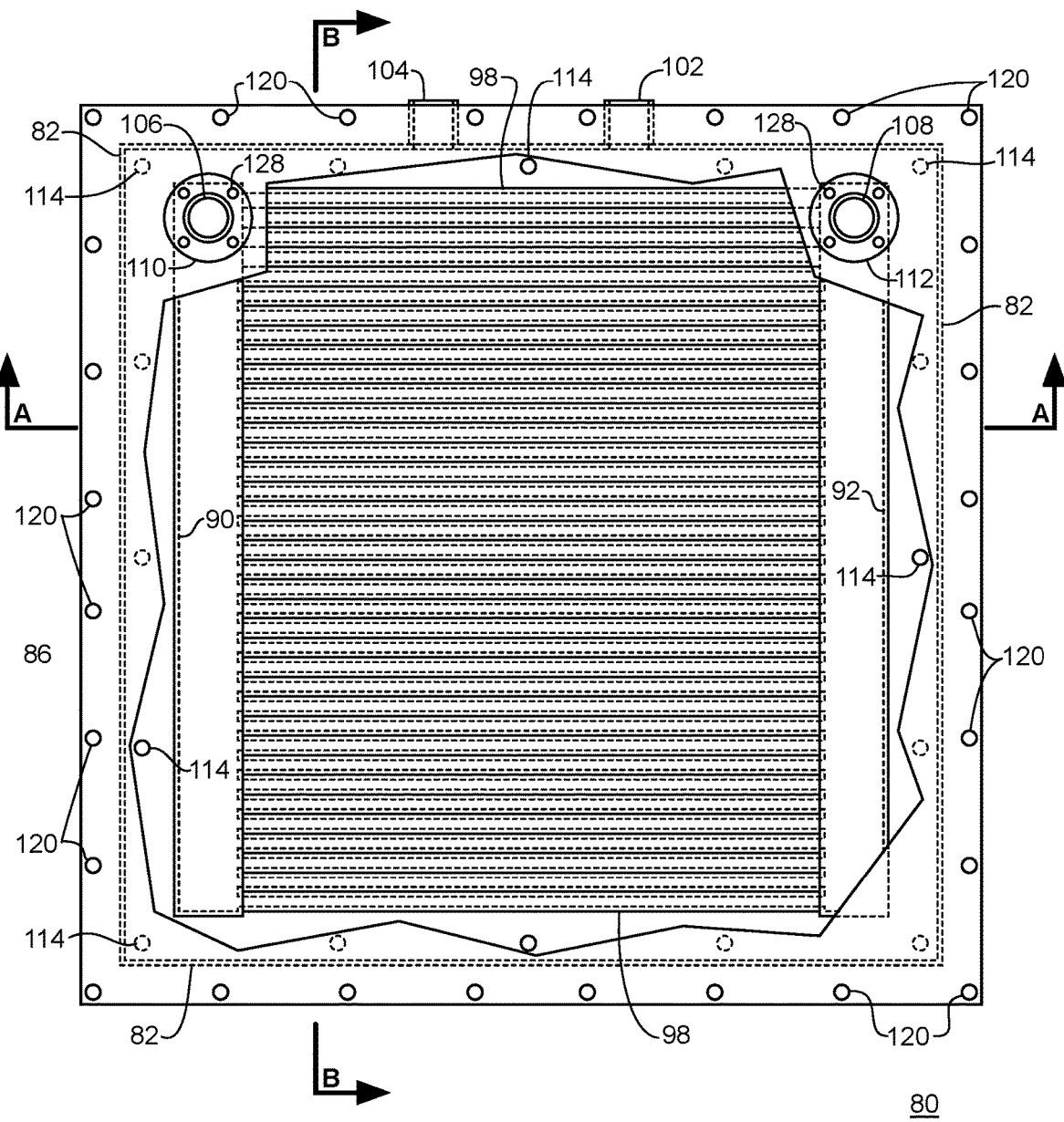
FIG. 5 is a front view drawing of a coolant tank and heat exchange assembly according to an illustrative embodiment of the present invention.
Figure 6:
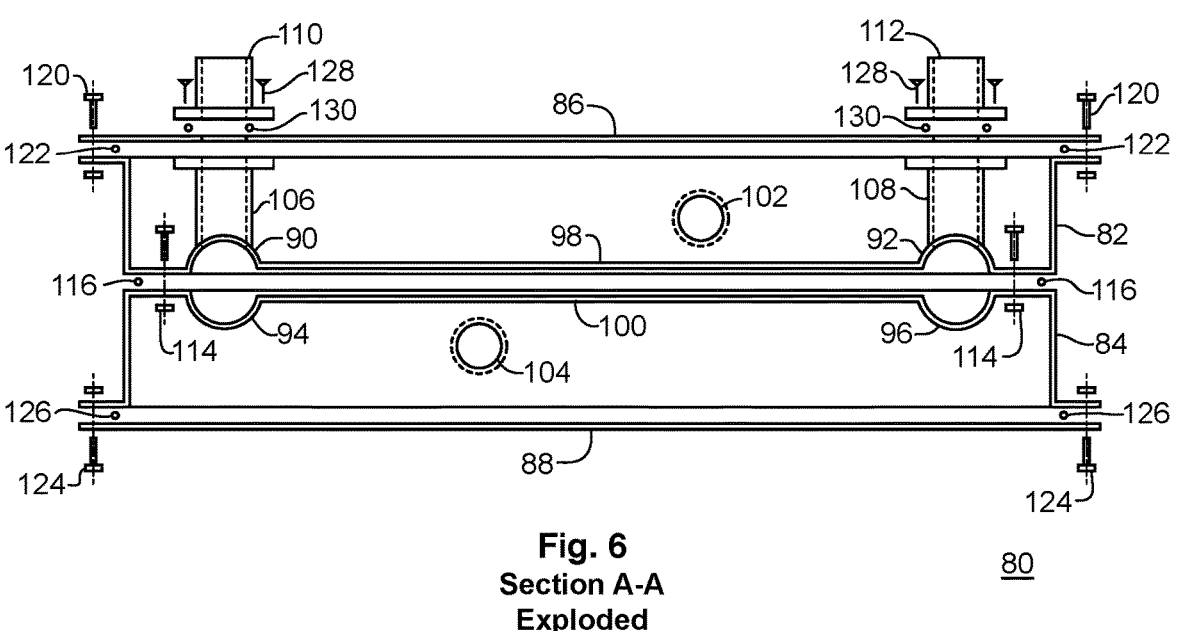
FIG. 6 is an exploded section view drawing of a coolant tank and heat exchange assembly according to an illustrative embodiment of the present invention.
Figure 7:
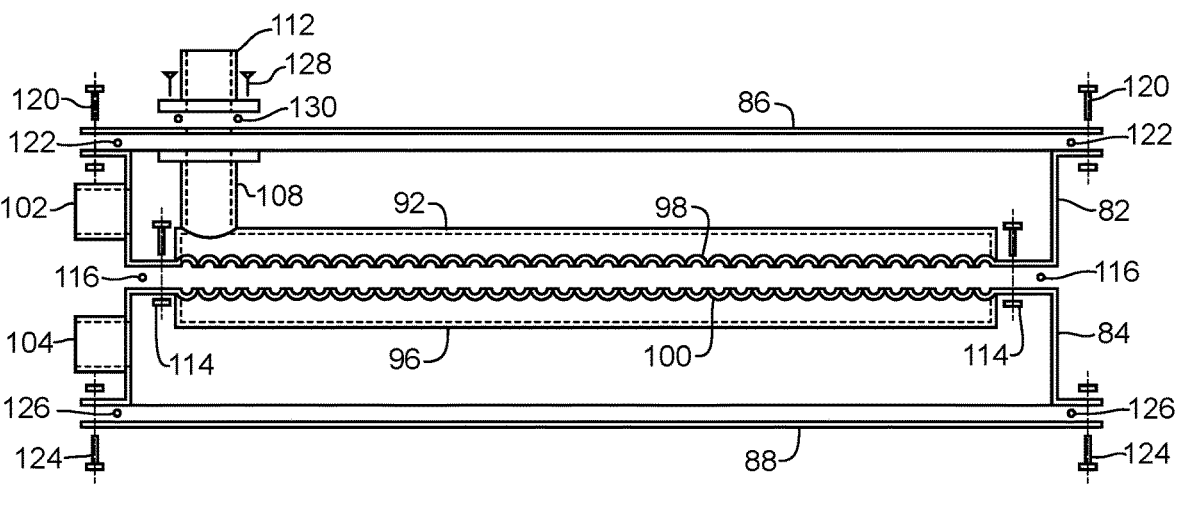
FIG. 7 is an exploded section view drawing of a coolant tank and heat exchange assembly according to an illustrative embodiment of the present invention.

Reference is directed to FIG. 4, which is a functional block diagram of a cold therapy system according to an illustrative embodiment of the present invention. FIG. 4 corresponds with FIG. 3. In FIG. 4, the cold therapy apparatus 19 is presented, but with the coolant heat exchange assembly 57 removed from the insulated enclosure 70, and placed into a freezer 74, or other cold environment. After a period of time, the coolant 60 temperature will stabilize at the freezer 74 temperature and be ready for reconnection to the cold therapy apparatus 19. Note that the user of such an apparatus may be provided with two or more coolant heat exchange assemblies 57, 59, such that they can be rotated in service between cold therapy use and a freezer to 'recharge' for subsequent use.

Reference is directed to FIGS. 5, 6, 7, 8, and 9, which are a front view drawing, exploded section view drawings, and section view drawings, as indicated, of a coolant heat exchange assembly 80 according to an illustrative embodiment of the present invention. One aspect of the apparatus and methods of the present disclosure is the requirement to provide a cost effective cold therapy apparatus in view of prior art designs, but that also provides improved performance. The design of the coolant heat exchange assembly 80 represents one opportunity to achieve these objectives. The coolant heat exchange assembly 80 is low cost because it is molded of a few thermoplastic moldings that are conveniently sealed and joint together in a manner not formerly utilized in such devices. In the illustrative embodiment, that thermoplastic is high density polyethylene (HDPE). HDPE has good molding characteristics, low cost, and has exhibited useful thermal transfer properties between the coolant and thermal fluid within the heat exchanger portion of the coolant heat exchange assembly 80. Other thermoplastics can be employed, including acrylonitrile butadiene styrene (ABS), polycarbonate, polyether sulfone, polyethylene, polypropylene, polyvinyl chloride, polyvinylidene fluoride, and others.

Figure 8:
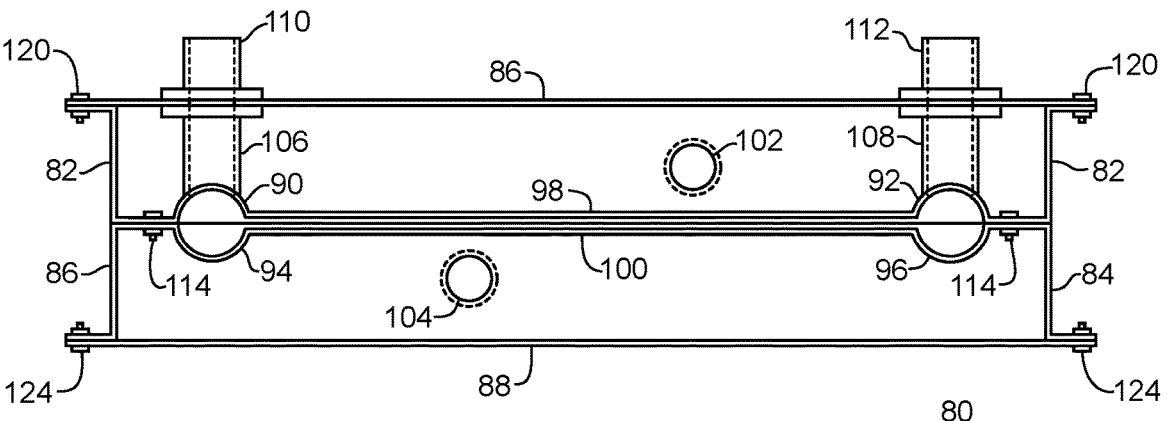
FIG. 8 is a section view drawing of a coolant tank and heat exchange assembly according to an illustrative embodiment of the present invention.
Figure 9:
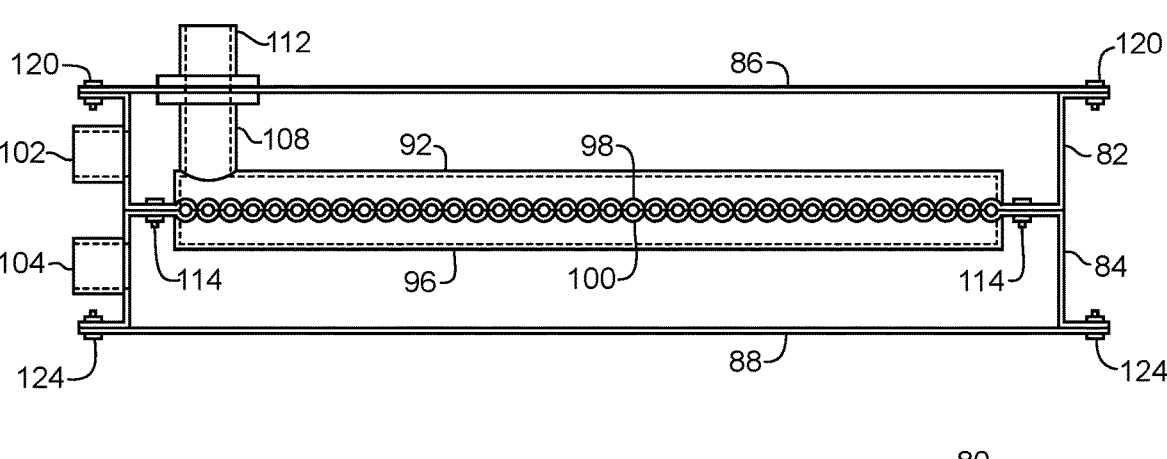
FIG. 9 is a section view drawing of a coolant tank and heat exchange assembly according to an illustrative embodiment of the present invention.

The heat exchanger and the coolant tank are formed together by assembling the several moldings illustrated in FIGS. 5 through 9. The heat exchanger is formed by joining two moldings 82, 84, which are formed to define opposing halves of plural heat exchange tubes 98, 100, and opposing halves of the outlet manifold 90, 94, and the inlet manifold 92, 96, which fluidly coupled with the plural heat exchange tubes 98, 100, as illustrated. An O-ring seal 116 is disposed between these two moldings 82, 84, and then the moldings 82, 84 are joined in clamshell fashion with plural mechanical fastener sets 114 to define the completed heat exchanger as illustrated in FIGS. 8-9. The fasteners can be any suitable fastener, and in this illustrative embodiment screw and nut sets 114 are utilized. Alternatively, screws that engage polymeric bosses in the opposing side of the molding can cut threads therein and secure them together. The outlet manifold 90, 94 is coupled to an outlet conduit 106, and the inlet manifold 92, 96 is coupled to inlet conduit 108, and these are molding with molding 82. Note that the perimeter of the moldings 82, 86 include sidewalls with flanges, as illustrated, to define a volumetric space which serves as a first and second coolant tank portion. The coolant tank portions are then fully enclosed by coolant tank covers 86, 88.

In FIGS. 5 through 9, the two coolant tank portions are defined by moldings 82, 84 and covers 86, 88. Each portion includes a coolant fill port 102, 104 through the side walls of moldings 82, 84, which provide a means for filling with coolant. The covers 86, 88 are joined with moldings 82, 84 using plural mechanical fasteners 120, which are the same as the mechanical fasteners 114, in that screw and nut sets, or screw and boss connections can be employed. The covers 86 and 88 are also sealed using O-rings 122, 126, respectively, about their perimeters, as illustrated. The inlet and outlet conduits 106, 108 align with outlet couplers 110, 112, respectively, through holes in cover 86. These conduits and couplers are joined with flanges sealed with O-rings 130, and mechanical fasteners 128, as illustrated. With this assembled arrangement, the heat exchanger is fluidly coupled from the inlet coupler 112, through the inlet manifold 92, 96, through the plural heat exchange tunes 98, 100, through the outlet manifold 90, 94, and out the outlet coupler 110. And the two portions of the coolant tanks are defined by the moldings 82, 84 and covers 86, 88, as illustrated. The heat exchanger is fully immersed in the coolant during operation, with a first portion on one side and a second portion on the other side.

Figures 10A, 10B, 10C, 11A, 11B, 11C, 12A, 12B, 12C:
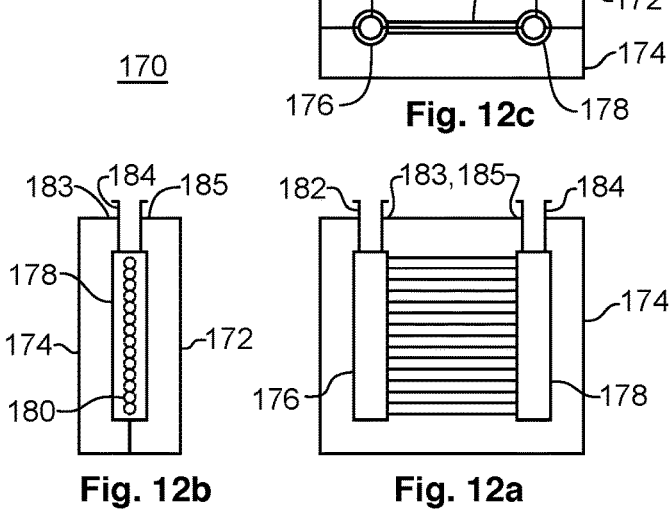
FIGS. 10*a*, 10*b*, and 10*c* are front, side, and end section view drawings of a coolant tank and heat exchange assembly according to an illustrative embodiment of the present invention.
FIGS. 11*a*, 11*b*, and 11*c* are front, side, and end section view drawings of a coolant tank and heat exchange assembly according to an illustrative embodiment of the present invention.
FIGS. 12*a*, 12*b*, and 12*c* are front, side, and end section view drawings of a coolant tank and heat exchange assembly according to an illustrative embodiment of the present invention.

Reference is directed to FIGS. 10a, 10b, and 10c, which are front, side, and end section view drawings of a coolant heat exchange assembly 130 according to an illustrative embodiment of the present invention. These drawings illustrate one orientation of the inlet conduit 144 and outlet conduit 142 through the cover area 135 of the assembly 130. Note the orientation of the heat exchange tubes 138, the inlet manifold 140, the outlet manifold 136, and the two coolant tank portions 132, 134.

Reference is directed to FIGS. 11a, 11b, and 11c, which are front, side, and end section view drawings of a coolant heat exchange assembly 150 according to an illustrative embodiment of the present invention. These drawings illustrate another orientation of the inlet conduit 164 and outlet conduit 162 through an end wall portion 163 of the assembly 150. Note the orientation of the heat exchange tubes 160, the inlet manifold 158, the outlet manifold 156, and the two coolant tank portions 152, 154.

Reference is directed to FIGS. 12a, 12b, and 12c, which are front, side, and end section view drawings of a coolant heat exchange assembly 170 according to an illustrative embodiment of the present invention. These drawings illustrate another orientation of the inlet conduit 184 and outlet conduit 182 through two end wall portions 183, 185 of the two coolant tank portions 172, 174 of the assembly 170. Note the orientation of the heat exchange tubes 180, the inlet manifold 178, the outlet manifold 176, and the two coolant tank portions 172, 174.

Figures 13A, 13B:
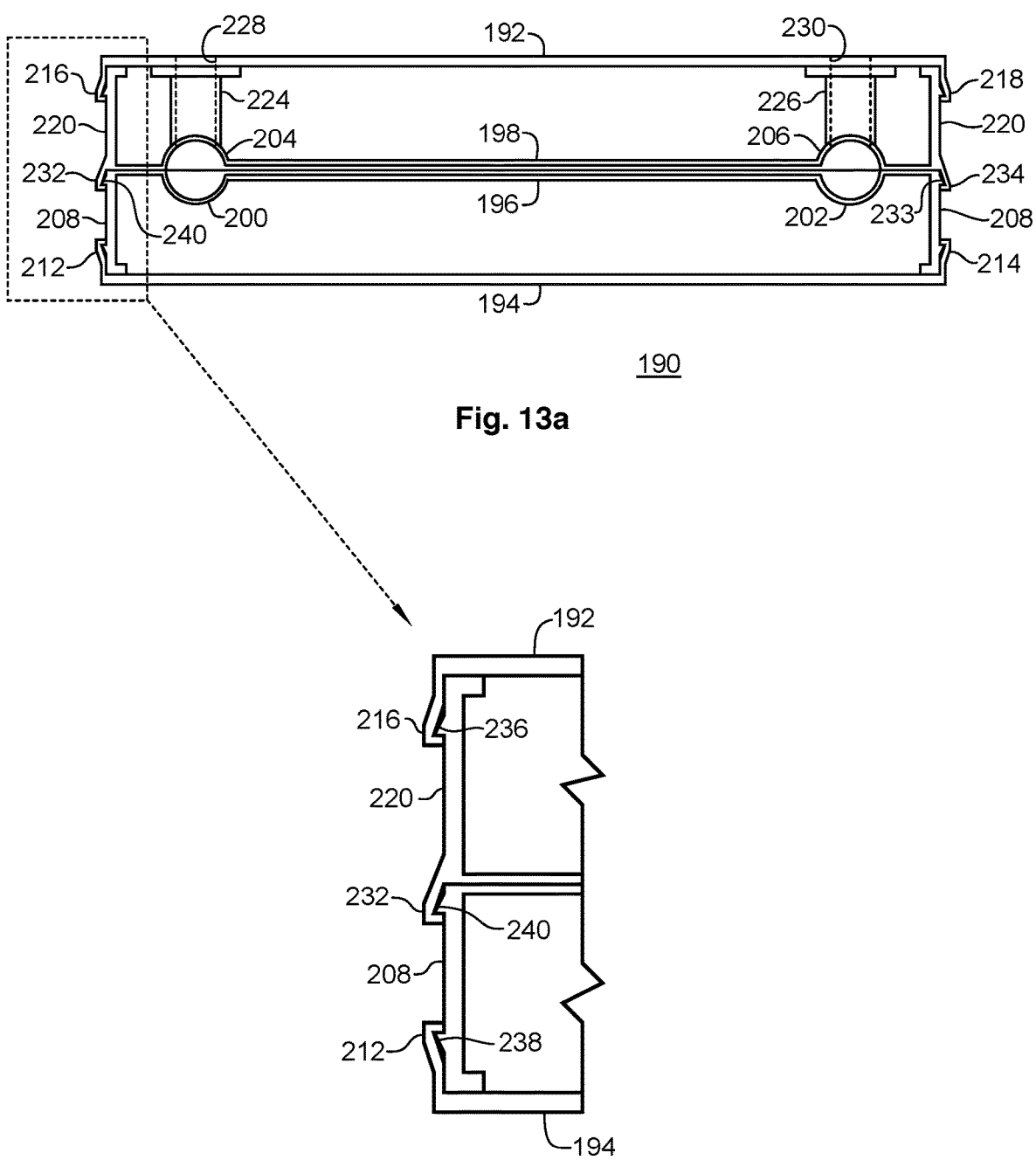
FIGS. 13*a* and 13*b* are a section view drawing and a detailed section view drawing, respectively, of a coolant tank and heat exchange assembly according to an illustrative embodiment of the present invention.

Reference is directed to FIGS. 13a and 13b, which are a section view drawing and a detailed section view drawing, respectively, of a heat exchanger assembly 190 according to an illustrative embodiment of the present invention. In the prior embodiments, mechanical fasteners were employed to join the various moldings together. In this embodiment, spring clips and cooperatively aligned lugs, which are molded together with the various moldings, are employed, thereby eliminating the need and costs associated with separate mechanical fasteners. In FIG. 13a, an upper molding 220 and a lower molding 208 are joined together. These moldings define the plural heat exchange tubes 196, 198, the inlet manifold 206, 202, the outlet manifold 204, 200, as well as the inlet conduit 226 and outlet conduit 224, in similar fashion as the previously discussed illustrative embodiments. On the right side of moldings 220, 208 is a spring clip 234 and cooperatively aligned lug 233. On the left side of these moldings is a spring clip 232 and cooperatively aligned lug 240. As the two moldings 220, 208 are joined together, the spring clips 234, 232 ride over their respective lugs 233, 240 and snap together. The spring action results from the elastic characteristic of the thermoplastic from which the moldings 220, 208 are formed.

In FIG. 13a, the upper cover 192 has spring clips 216, 218 illustrated on its left and right side, and, the lower cover 194 has spring clips 212, 214 illustrated on its left and right sides. There are spring clips located all about the periphery of these covers 192, 194 (not shown). The upper cover 192 also has holes formed therethrough 228, 230, aligned with the inlet conduit 226 and outlet conduit 224. FIG. 13b illustrates the cooperative arrangement of the spring clips and lugs. In particular, the upper molding 220 has spring clip 232, which aligns with cooperative lug 240 on the lower molding 208. The upper cover 192 has spring clip 216, which aligns with cooperative lug 236 on the upper molding 220. Similarly, the lower cover 194 has spring clip 212, which aligns with cooperative lug 238 on the lower molding 208. With this arrangement, the entire coolant heat exchange assembly 190 can be 'snapped' together without the use of separate mechanical fasteners. Also note that seals (not shown), such as O-ring seals, as disposed between the several moldings to prevent leakage of the coolant and thermal fluid.

Figures 14A, 14B, 14C:
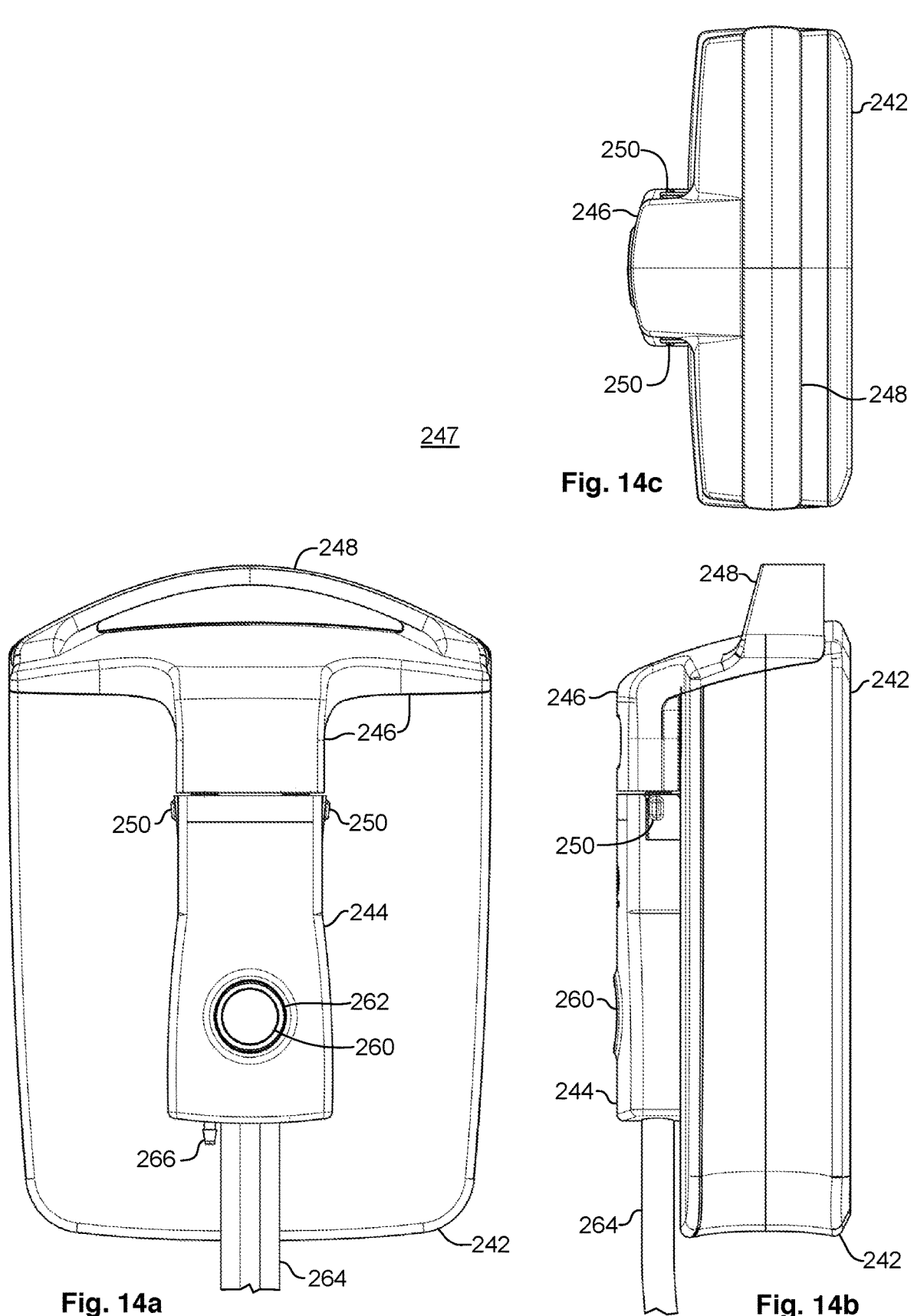
FIGS. 14*a*, 14*b*, and 14*c* are front view, side view, and end view drawings, respectively, of a cold therapy apparatus according to an illustrative embodiment of the present invention.

Reference is directed to FIGS. 14a, 14b, and 14c, which are front view, side view, and end view drawings, respectively, of a cold therapy apparatus 247 according to an illustrative embodiment of the present invention. These exterior views illustrate the insulated enclosure 242 with an upper insulated portion 246, which encloses a coolant heat exchange assembly (not shown) therein. The upper portion 246 includes a carry handle 248 for user convenience. A control unit 244 engages the upper insulated portion 246, which conceals a pair of thermal fluid couplers (not shown), and is selectively releasable with spring releases 250. The control unit 244 includes an actuator 260 for engaging operation of a pump (not shown) therein, as well as a timer function for controlling the duration of cold therapy. A ring of LED lights 262 encircle the actuator 260, and sequentially illuminate to indicate the during of therapy. In one embodiment, there are four LEDs in the circle, each indicating seven and one-half minutes of a thirty minute therapy session. A hose fitting 266 is presented on the control unit 244 for filling the coolant heat exchange assembly (not shown) and the umbilical tubing assembly 264, with thermal fluid. In other embodiments, hose couplers (not shown) are separated to provide access to fill with thermal fluid. In either configuration, a pump (not shown) in the control unit 244 provides the motive force for circulating thermal fluid into, and air out of, the thermal fluid tubing circuit.

Figure 15:
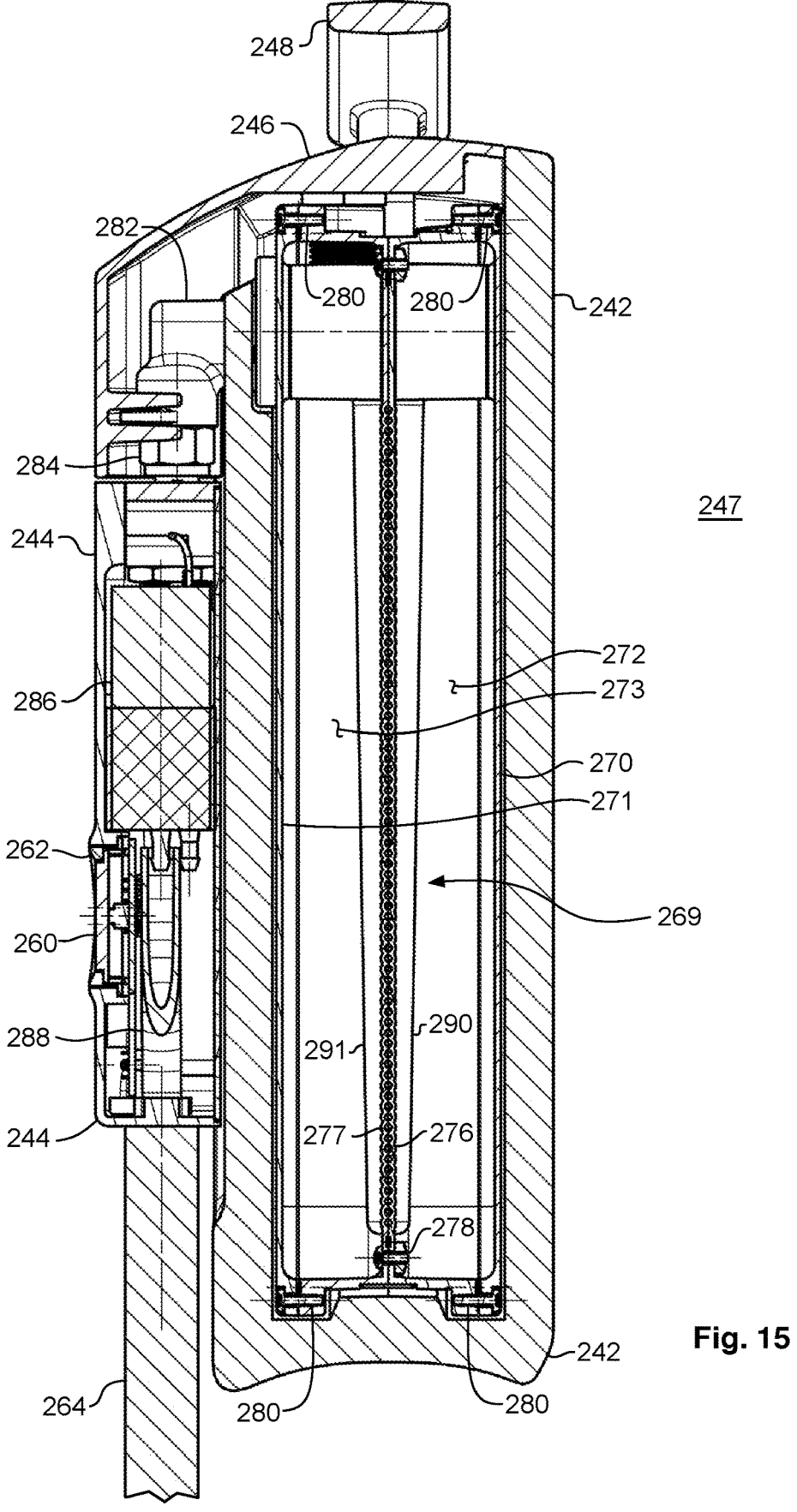
FIG. 15 is a section view drawing of a cold therapy apparatus according to an illustrative embodiment of the present invention.

Reference is directed to FIG. 15, which is a section view drawing of a cold therapy apparatus 247 according to an illustrative embodiment of the present invention. The insulated enclosure 242 and insulated upper portion 246, with carry handle 248, enclose the coolant heat exchange assembly 269. The heat exchanger is located within the coolant heat exchange assembly 269, and is assembled in clamshell fashion, with two halves. In particular, the plural heat exchange tubes 276, 277 are fluidly coupled to a thermal fluid manifold 290, 291, which is fluidly coupled to an elbow fitting 282. Of course, there are both inlet and outlet manifolds and fittings, but only one side is visible in this section view. A thermal fluid coupler 284 is connected to the elbow fitting 282, and serves as a point of connection for the control unit 244. The coolant heat exchange unit 269 is formed to two halves 272, 273 and covers 270, 271 to define two coolant tank portions. The halves 272, 273 are joined with plural mechanical fasteners 278 about their peripheries, and, the covers 270, 271 are joined with the halves 272, 273 with plural mechanical fasteners 280 about their peripheries.

The control unit 244 in FIG. 15 includes a pump 286, which is a diaphragm pump in the illustrative embodiment. The control actuator 260 with LED ring light 262, are presented on the exterior of the control unit 244. Internal tubing 288 connects the thermal fluid circuit, which couples to the umbilical tube assembly 264.

Figure 16:
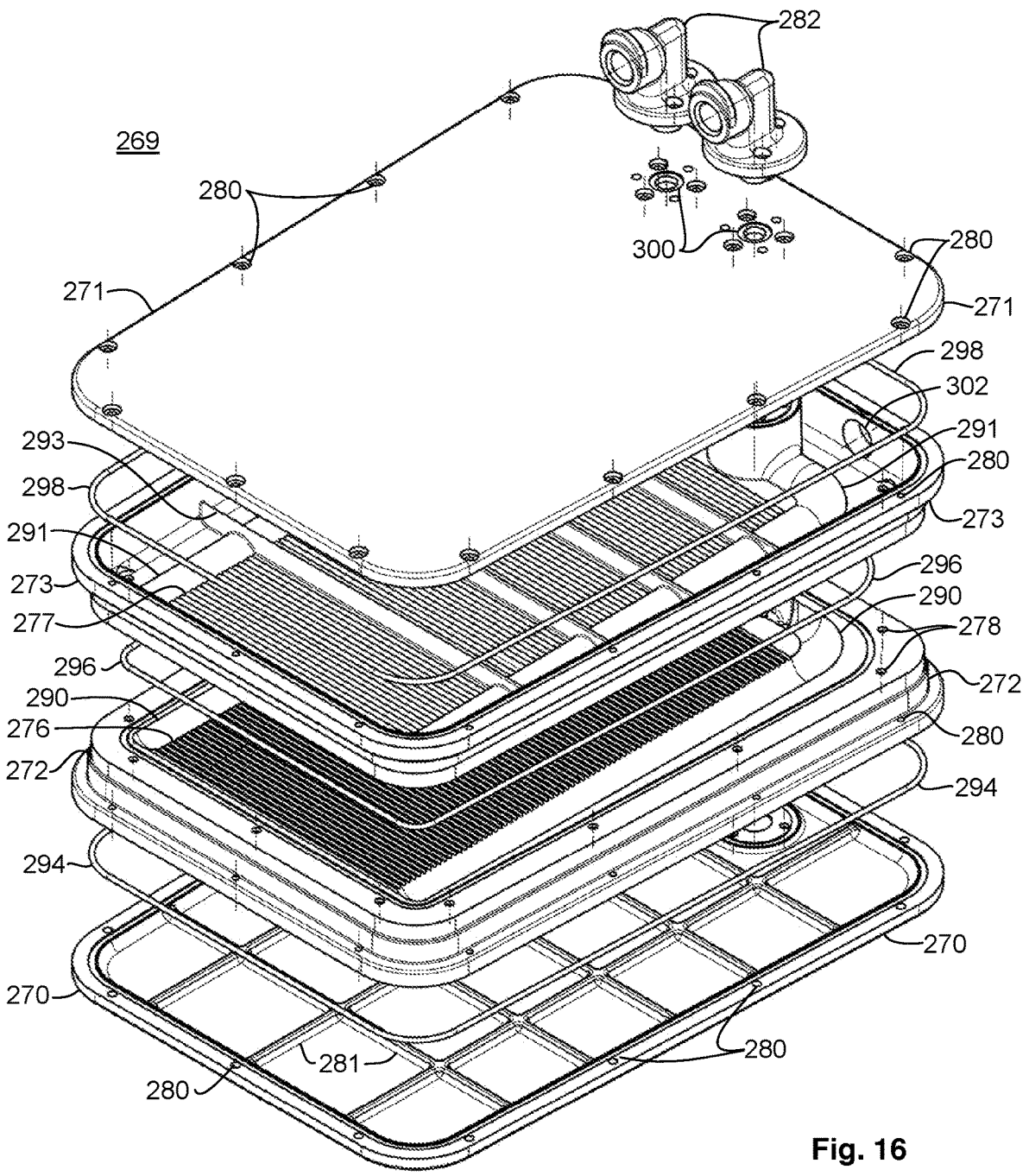
FIG. 16 is an exploded isometric view drawing of a coolant tank and heat exchange assembly according to an illustrative embodiment of the present invention.

Reference is directed to FIG. 16, which is an exploded isometric view drawing of a heat exchanger assembly 269 according to an illustrative embodiment of the present invention. Beginning from the bottom of the drawing sheet, the components of the coolant heat exchange assembly 269 include the lower coolant cover 270 ("lower cover"), the lower O-ring seal 294, the lower coolant tank and heat exchanger molding 272 ("lower molding"), the middle O-ring seal 296, the upper coolant tank and heat exchanger molding 273 ("upper molding"), the upper O-ring seal 298, and the upper coolant tank cover 271 ("upper cover"), as illustrated. The lower cover 270 has plural mechanical fastener holes 280 about it perimeter, and stiffening ribs 281 on its interior surface. The lower O-ring 294 is routed about the perimeter of the lower cover 270. The lower molding 272 also has plural mechanical fastener holes 280 about its perimeter, and a second set of mechanical fastener holes 278 about its perimeter as well. The lower molding 272 includes half of the plural heat exchange tubes 276 and half of the thermal fluid manifolds 290 formed integral with it. The upper molding 273 also has plural mechanical fastener holes 280 about its perimeter. The upper molding 273 includes the other half of the plural heat exchange tubes 277 and the other half of the thermal fluid manifolds 291 formed integral with it. A coolant fill port 302 is proved through upper molding 273 for filling the coolant tank with coolant prior to use. The upper molding 273 also illustrates stiffening ribs 293 to reinforce it against pressure forces. The upper cover 271 has plural mechanical fastener holes 280 form through it, as well as manifold connection and fluid channels 300 formed into it. A pair of fluid elbows 282 are provided for connection to the thermal fluid inlet and outlet couplers (not shown). Note that the covers and moldings are generally symmetrical to one another. For example, both the upper and lower items have stiffening ribs even though they may not be visible in this isometric view. Both of the upper and lower molding also have coolant fill ports 302. The mechanical fastener holes 280 attach the covers to the moldings, and the mechanical fastening holes 278 attach the upper and lower moldings 272, 273 to one another.

Figures 17A, 17B, 17C:
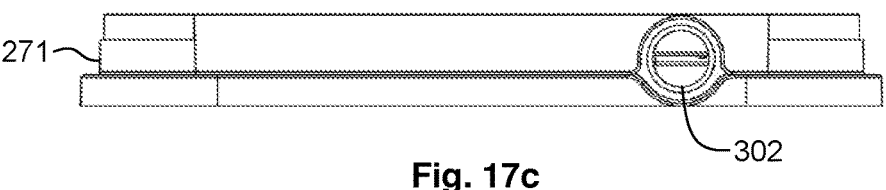
FIGS. 17*a*, 17*b*, and 17*c* are front view, side section view, and end view drawings, respectively, of a coolant tank and heat exchange molding according to an illustrative embodiment of the present invention.

Reference is directed to FIGS. 17a, 17b, and 17c, which are front view, side section view, and end view drawings, respectively, of the upper coolant tank and heat exchange molding 271 according to an illustrative embodiment of the present invention. The plural mechanical fastener holes 280 about the perimeter are shown, as well as the second set of mechanical fastening holes 278 just inside of the first set. The thermal fluid manifold 291 can bee seen, with the plural heat exchange members 277 visible as well. The manifolds 291 terminate with a fluid riser 310. Stiffening ribs 306, 308 are provided to reinforce against pressure loads during operation. The coolant fill port 302 is also shown.

Figures 18A, 18B:
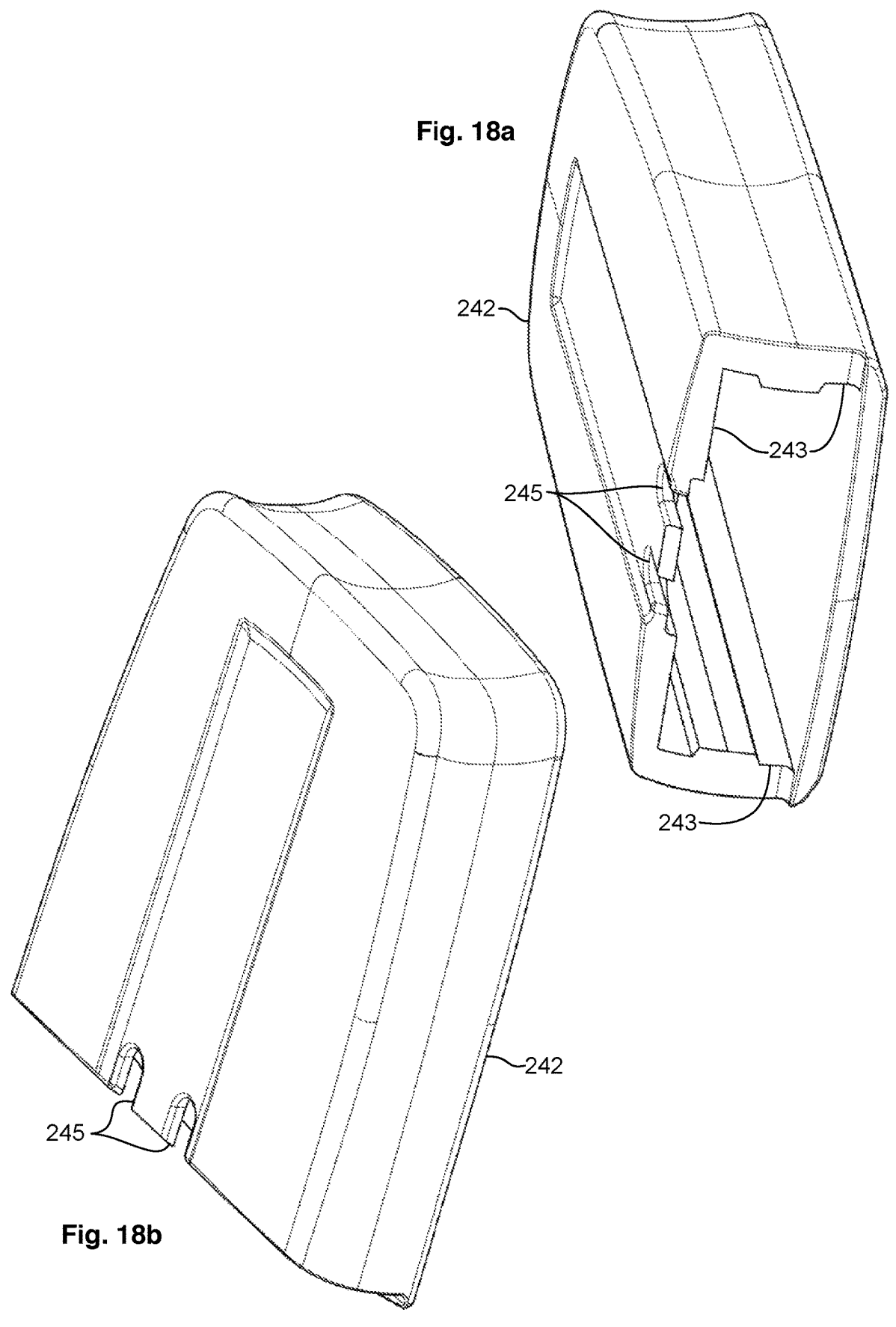
FIGS. 18*a* and 18*b* are isometric view drawings of an insulated enclosure according to an illustrative embodiment of the present invention.

Reference is directed to FIGS. 18a and 18b, which are isometric view drawings of an insulated enclosure 242 according to an illustrative embodiment of the present invention. The insulated enclosure 242 serves to insulate the coolant heat exchange unit (not shown) from external sources of heat. Any suitable cellular of fibrous polymeric material may be employed, provided that it as sufficient rigidity to maintain its shape and can engages a cosmetically suitable exterior surface, such as paint. An opening 243 at one end receives the coolant heat exchange unit (not shown). Recesses 245 are provided for passage of the thermal fluid conduits, tubes, or fittings.

Figure 19:
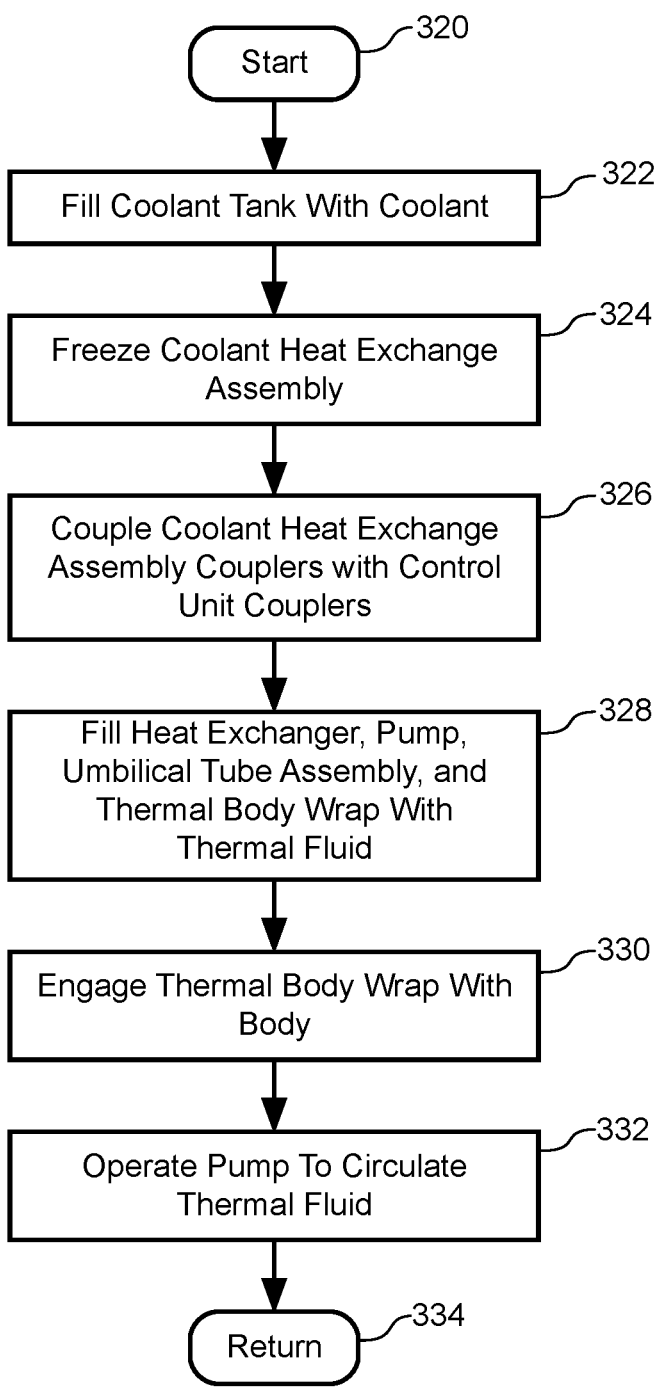
FIG. 19 is a process flow diagram according to an illustrative embodiment of the present invention.

Reference is directed to FIG. 19, which is a process flow diagram showing operation of the subject apparatus by an end user and according to an illustrative embodiment of the present invention. The process starts at step 320 and proceeds to step 322 where the coolant tank is filled through the coolant fill ports with coolant. At step 324, the coolant heat exchange assembly is placed into a freezer for a sufficiently long enough time so that the coolant reaches freezer temperature. At step 326, the coolant heat exchanger is placed into the insulated enclosure and the control unit is coupled to it using the thermal fluid couplers. At step 328, the heat exchanger, pump, umbilical tubing and thermal body wrap are filled with thermal fluid from a separate container using the pump to circulate it. At step 330, the thermal body wrap is engaged with a selection part of the user's body. At step 332, the pump is operated to circulate the thermal fluid, thereby transferring heat from the user's body, into the thermal fluid, and subsequently exchanged into the coolant by the heat exchanger. The process returns at step 334, to be repeated as necessary. In an alternative method, the thermal fluid may be circulated into the coolant and heat exchange unit prior to placing into a freezer such that the volume of thermal fluid that fills the inlet and outlet manifolds and heat exchange tubes is also reduced to freezer temperatures. This approach provides an incremental amount of cooling capacity.

In certain embodiments of the present invention, the thermal body wrap is provided in a new and fully collapsed condition, and well as the entire coolant heat exchange assembly being provided empty of thermal fluid. Although, the coolant is often times provided within a new unit, in a hermetically sealed condition. As such, it is incumbent on the user to fill the coolant heat exchange assembly and thermal body wrap with thermal fluid prior to initial operation. In certain embodiments, presented below, a thermal fluid fill port is provided so that user can pour thermal fluid into the unit. The internal pump is started, which circulates the thermal fluid through the entire system, including the thermal body wrap. The thermal fluid is poured into a thermal fluid reservoir, which contains sufficient volume to complete the initialization. It should be noted that the empty thermal body wrap must be 'inflated' with thermal fluid to commence operation, which results in a portion of the thermal fluid being removed from such a reservoir. This action may create suction starvation to the pump, which cannot then prime it self for proper operation. In addition, the volumetric void created by transferring the thermal fluid from the reservoir to the body wrap must be addressed. The following disclosure addresses them problems in the art.

Figure 20:
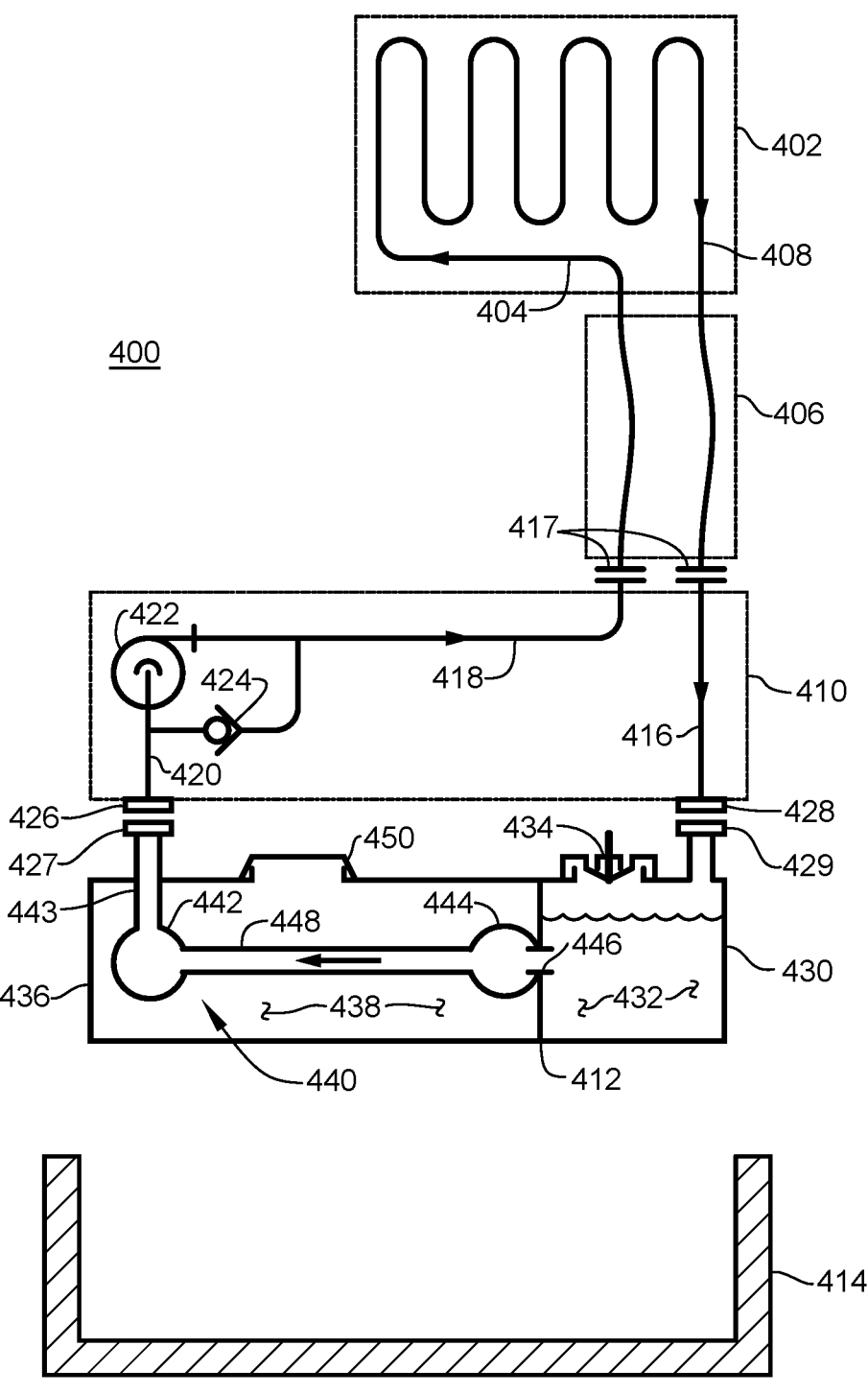
FIG. 20 is a fluid diagram of a cold therapy apparatus according to an illustrative embodiment of the present invention.

Reference is directed to FIG. 20, which is a fluid schematic diagram of a cold therapy apparatus 400 according to an illustrative embodiment of the present invention. This embodiment principally differs from those hereinbefore described in that a thermal fluid reservoir 430 is added to the thermal fluid circuit, which circuit comprises a thermal body wrap 402, an umbilical tube assembly 406, a control unit 410 with thermal fluid pump 422, a heat exchanger 440, and the thermal fluid reservoir 430. The thermal fluid reservoir 430 may also include a vacuum relief valve 434, which is useful for efficient start-up by facilitating initial 'inflation' of an empty and collapsed thermal body wrap 402. The control unit 410 may include a pressure relief valve 424 that bypasses the pump 422 outlet back to its inlet, which serves to limit the maximum pressure delivered to the thermal body wrap 402 and thereby protects it from possible stress damage and rupture.

The thermal body wrap 402 and umbilical tube assembly 406 may be provided as an integral unit with suitable couplers 417 presented for connection to the rest of the system components. A coolant fluid inlet tube 404 routes through the body wrap 402 to a thermal fluid outlet tube 408, as generally illustrated in FIG. 20. Within the control unit 410, the coolant fluid inlet tube 404 is coupled to a pump outlet tube 418, and the thermal fluid outlet tube 408 is coupled to a thermal fluid through-tube 416 that is connected to a thermal fluid return coupler 428. A thermal fluid inlet coupler 426 is connected to the pump 422 inlet through tube 420. The aforementioned pressure relief valve 424 is connected between the pump 422 inlet and outlet. The pressure rating of the pressure relief valve 424 is selected to be somewhat less than the thermal wrap 452 maximum working pressure. A coolant heat exchange assembly 412 comprises a coolant tank 436 with heat exchanger 440 therein, and a thermal fluid reservoir 430. The coolant tank is filled with coolant 438 and the thermal fluid reservoir 430 contains thermal fluid 432, and typically some air that enters through the the vacuum relief valve 434. Also note, in FIG. 20, that the insulated housing 414 for the heat exchange assembly 412 is illustrated, and the coolant heat exchange assembly 412 is inserted int the insulated housing 414 prior to operation.

The coolant heat exchange assembly 412 receives thermal fluid 432 through a thermal fluid inlet coupler 429, which is selectively engaged with the control unit thermal fluid return coupler 428. Similarly, the coolant heat exchange assembly 412 delivers chilled thermal fluid 432 through a thermal fluid outlet coupler 427, which is selectively engaged with the control unit thermal fluid supply coupler 426. The selective coupling arrangement enables the user to swap plural coolant heat exchange assemblies 412 between chilling in a refrigerated environment and use in on-body thermal therapy. In the illustrative embodiment of FIG. 20, the thermal fluid returns from the body wrap 402 into the thermal fluid reservoir 430 through the thermal fluid inlet coupler 429, and then flows into a heat exchange 440 through a thermal fluid drain 446, which us located below the thermal fluid 432 liquid level in the thermal fluid reservoir 430 so that only liquid enters the heat exchanger 440. The thermal fluid passes through the drain 446 enters an inlet manifold 444 of the heat exchanger 440, and passes through plural heat exchange tubes 448 into an outlet manifold 442. It is within the plural heat exchange tubes that the bulk of the heat transfer from the coolant 438 to the thermal fluid 432 occurs. The outlet manifold is coupled through a riser 443 the thermal fluid outlet coupler 427. The coolant tank 436 includes a sealed fill port 450 for charging the system with coolant, which is typically done at the time of manufacturer and not by the user. The thermal fluid reservoir is filled through an opening for the vacuum relief valve 434, which is arranged as a removable coolant tank cap in the illustrative embodiment During initial start-up of the thermal fluid circuit, the body wrap 402 will typically be empty and devoid of fluids, which may effect pump 422 operation in that the heat exchange assembly 440 is 'starved' for suction since the body wrap 402 is deflated into itself. This 'starved' condition is communicated by fluid coupling to the inlet of the pump 422, which may prevent the pump from priming and beginning the body wrap inflation process. To alleviate this potential issue, the vacuum relief valve 434 opens by virtue of differential pressures, in check valve fashion, to allow a small amount of air to enter the thermal fluid reservoir 430, thereby alleviating the suction-locked condition. The pump 422 may thusly begin pumping thermal fluid into the body wrap 402, thereby inflating it for operation. Once inflated, the suction lock condition is obviated, but a small amount of air will typically be present in the thermal fluid reservoir 430, as illustrated. Gravity provides a separating action between air and liquid, so that only liquid thermal fluid passes through the drain 446 into the heat exchanger 440 inlet manifold 444.

Figure 21:
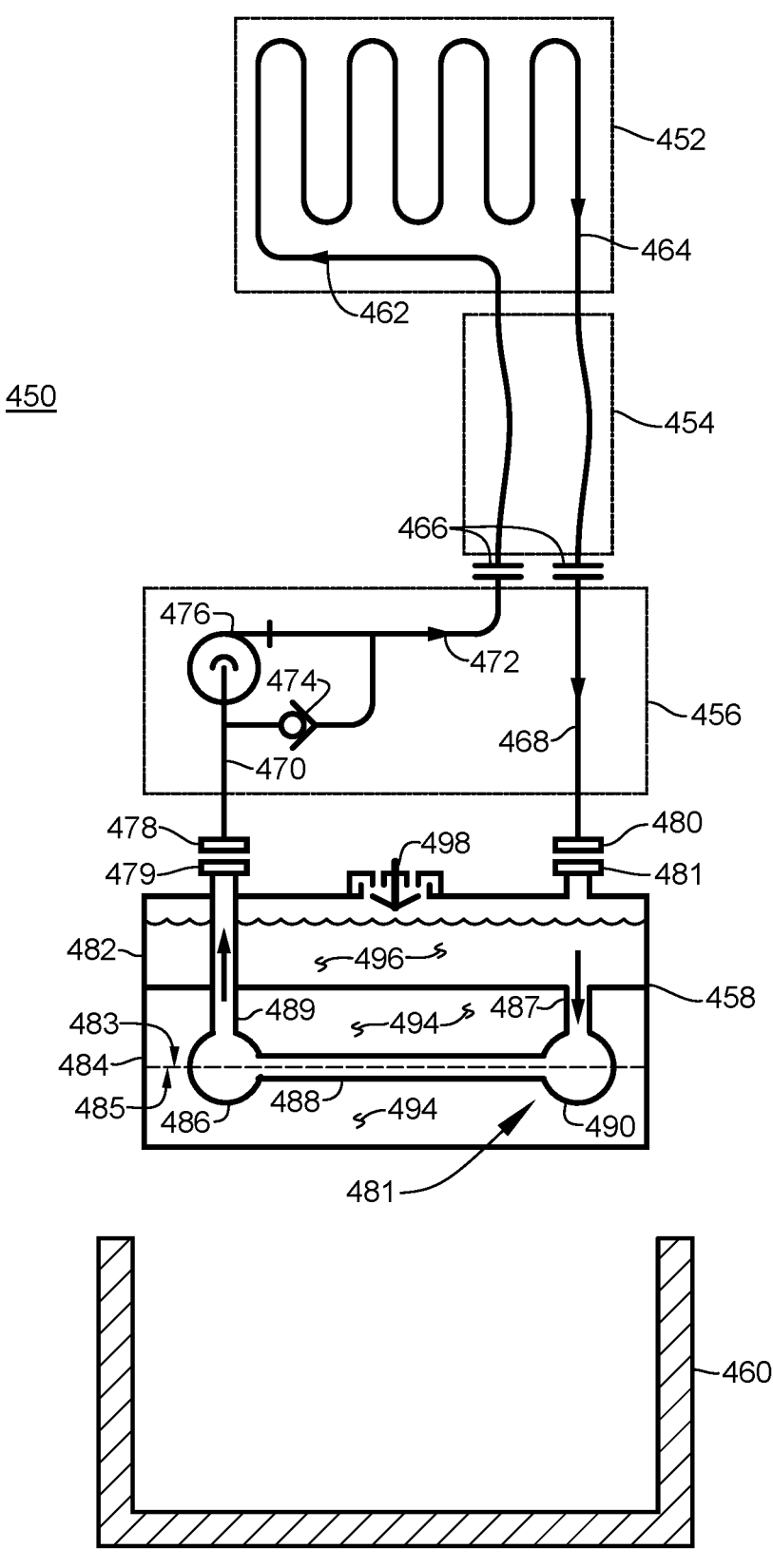
FIG. 21 is a fluid diagram of a cold therapy apparatus according to an illustrative embodiment of the present invention.

Reference is directed to FIG. 21, which is a fluid diagram of a cold therapy apparatus 450 according to an illustrative embodiment of the present invention. This embodiment also differs from those hereinbefore described in that a thermal fluid reservoir 482 is added to the thermal fluid circuit, which circuit comprises a thermal body wrap 452, an umbilical tube assembly 454, a control unit 456 with thermal fluid pump 476, a heat exchanger 481, and the thermal fluid reservoir 482. The thermal fluid reservoir 482 may also include a vacuum relief valve 498, which is useful in efficient start-up by facilitating initial 'inflation' of an empty thermal body wrap 452. The control unit 456 may include a pressure relief valve 474 that bypasses the pump 476 outlet back to its inlet, which serves to limit the maximum pressure delivered to the thermal body wrap 452 and thereby protects it from possible rupture.

The thermal body wrap 452 and umbilical tube assembly 454 may be provided as an integral unit with suitable couplers 466 presented for connection to the rest of the system components. A coolant fluid inlet tube 462 routes through the body wrap 452 to a thermal fluid outlet tube 464, as generally illustrated in FIG. 21. Within the control unit 456, the coolant fluid inlet tube 462 is coupled to a pump outlet tube 472, and the thermal fluid outlet tube 464 is coupled to a thermal fluid through-tube 468 that is connected to a thermal fluid return coupler 480. A thermal fluid inlet coupler 478 is connected to the pump 476 inlet through pump inlet tube 470. The aforementioned pressure relief valve 474 is connected between the pump 476 inlet and outlet. The pressure rating of the pressure relief valve 474 is selected to be somewhat less than the thermal wrap 452 maximum working pressure. A coolant heat exchange assembly 458 comprises a coolant tank 484 with heat exchanger 481 therein, and a thermal fluid reservoir 482 located above a coolant tank 484. The coolant tank 484 is filled with coolant 494 and the thermal fluid reservoir 482 contains thermal fluid 496, and typically some air that enters through the the vacuum relief valve 498. Also note, in FIG. 21, that the insulated housing 460 for the heat exchange assembly 458 is illustrated.

The coolant heat exchange assembly 458 receives thermal fluid 496 through a thermal fluid inlet coupler 481, which is selectively engaged with the control unit 456 thermal fluid return coupler 480. Similarly, the coolant heat exchange assembly 458 delivers thermal fluid 496 through a thermal fluid outlet coupler 479, which is selectively engaged with the control unit thermal fluid supply coupler 478. The selective coupling arrangement enables the user to swap plural coolant heat exchange assemblies between chilling in a refrigerated environment and use for on-body thermal therapy. In the illustrative embodiment of FIG. 21, the thermal fluid returns from the body wrap 452 into the thermal fluid reservoir 482 through the thermal fluid inlet coupler 481, and then flows into a heat exchange 481 through a thermal fluid drain 487, which drains into the thermal fluid reservoir 482. The thermal fluid passes through the drain 487 and enters an inlet manifold 490 of the heat exchanger 481, and passes through plural heat exchange tubes 488 into an outlet manifold 486. It is within the plural heat exchange tubes that the bulk of the heat transfer from the coolant 494 to the thermal fluid 496 occurs. The outlet manifold 486 is coupled through a riser 489, through the thermal fluid reservoir 482 and through the thermal fluid outlet coupler 479. The thermal fluid reservoir 482 is filled through the vacuum relief valve 498, which is arranged as a removable cap in the illustrative embodiment.

The coolant heat exchange assembly 458 in FIG. 21 is arranged in a stacked manner, where the enclosing components of the coolant tank 484, the heat exchanger 481, and the thermal fluid reservoir 482 share common sidewalls. The stacking of these components will be more fully discussed hereinafter, however note in FIG. 21 that a two sided seam 483, 485 exists where two halves of the heat exchanger 481 and coolant tank 484 are joined together, and sealed, to isolate the thermal fluid 496 inside the heat exchanger 481 from the coolant 494 inside the coolant tank 484. It will be appreciated that this arrangement yields a reliable and cost effective arrangement for mass production of products employing the novel advancements in the art taught through this embodiment.

During initial start-up of the thermal fluid circuit, the body wrap 452 will typically be empty and devoid of fluids, which may effect pump 476 operation in that the heat exchange assembly 458 is 'starved' for suction since the body wrap 452 is deflated into itself. This 'starved' condition is communicated by fluid coupling to the inlet of the pump 476, which may prevent the pump from priming and beginning the body wrap inflation process. To alleviate this potential issue, the vacuum receive valve 498 opens, in check valve fashion, to allow a small amount of air to enter the thermal fluid reservoir 482, thereby alleviating the suction-locked condition. The pump 476 can thusly begin pumping thermal fluid into the body wrap 452, thereby inflating it for operation. Once inflated, the suction lock condition is obviated.

Figure 22:
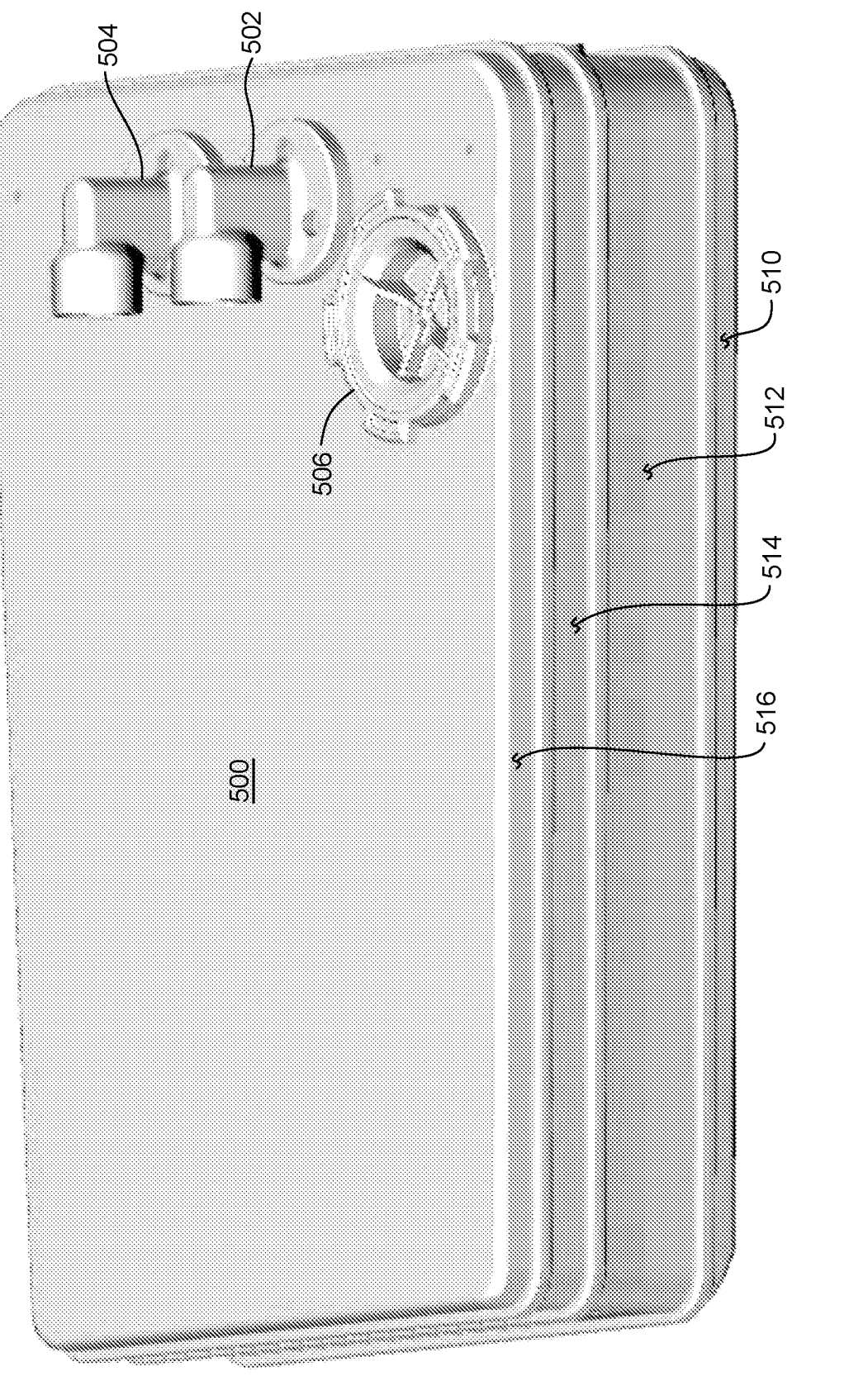
FIG. 22 is a perspective view drawing of coolant heat exchange assembly according to an illustrative embodiment of the present invention.

Reference is directed to FIG. 22, which is a perspective view drawing of coolant heat exchange assembly 500 according to an illustrative embodiment of the present invention. This embodiment illustrates the stacked arrangement of the various compartments in the coolant heat exchange assembly 500. Note that a thermal fluid inlet coupler 502 and a thermal fluid outlet coupler 504 are presented on the exterior of the assembly 500. So too is a vacuum relief valve and fill cap 506 illustrated. The fill cap function enables the user to periodically, and easily, fill the unit with the working thermal fluid. Since isopropyl alcohol is used as the working thermal fluid, it will eventually evaporate. Isopropyl alcohol is employed because of its low freezing point and antibacterial properties as the wraps can develop bacteria if they are not cleaned regularly. Looking along the side of the coolant heat exchange assembly 500, the locations of the lower coolant tank 510, the heat exchanger 512, the upper coolant tank 514, and the thermal fluid reservoir 516 are identified.

Figure 23A:
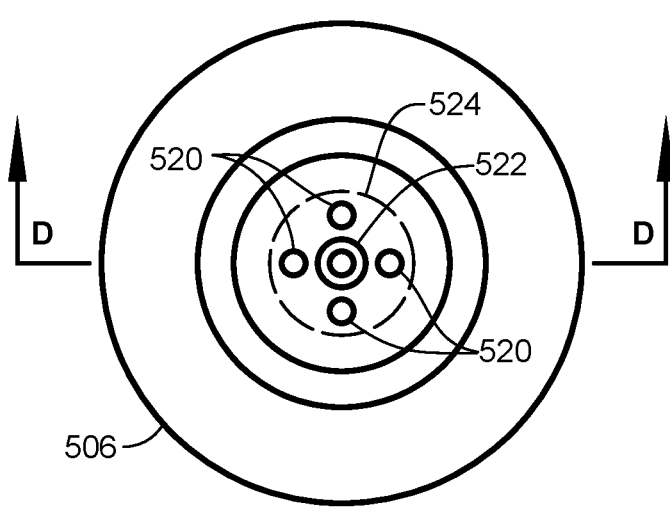
FIGS. 23A, 23B, and 23C are a front view drawing, and two section view drawings, respectively, of a vacuum relief valve according to an illustrative embodiment of the present invention.
Figure 23B:
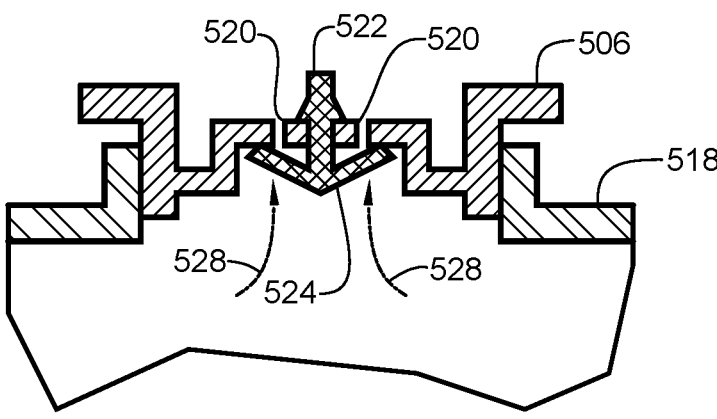
Figure 23C:
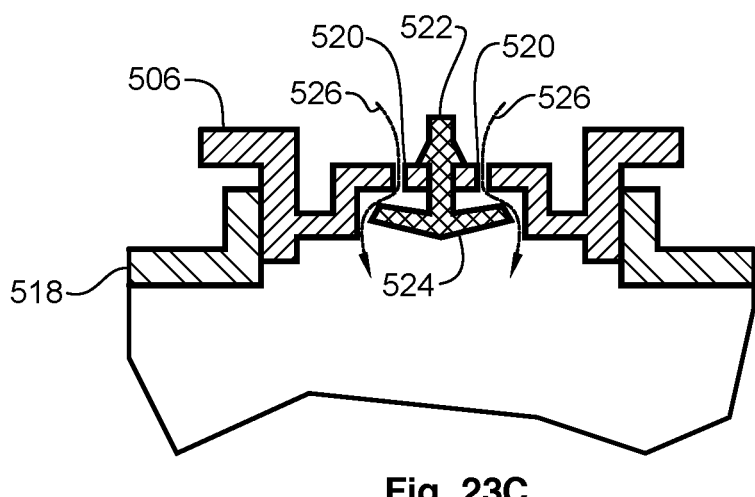

Reference is directed to FIGS. 23A, 23B, and 23C, which are a front view drawing, and two section view drawings, respectively, of a vacuum relief valve assembly according to an illustrative embodiment of the present invention. In the illustrative embodiment, the vacuum relief valve is fitted to a fill cap 506 that is theadably engaged with an opening in the thermal fluid reservoir 518. The fill cap 506 has one or more vent holes 520 formed therethrough, which enable the flow of air 526 into the reservoir 518 when the internal pressure is lower than atmospheric pressure, such as when the aforementioned pump (not shown) is suction starved. This mode and function is illustrated in FIG. 23C, where the air flows 526 around a resilient diaphragm 524, which is displaced away from the vent holes 520 by the movement 526 of the air. The resilient diaphragm 524 is retained in place by a resilient stem 522 that engages the fill cap 506, as illustrated. In the opposite condition, where the internal pressure is greater than the atmospheric pressure, the internal air or thermal fluid inside the reservoir 518 forces the resilient diaphragm against the vent holes 520, thereby sealing them closed. This mode of operation is illustrated in FIG. 23B, where the internal pressure 528 forces the diaphragm 524 against the vents 520. The fill cap can also be removed for adding thermal fluid to the reservoir.

Figure 24:
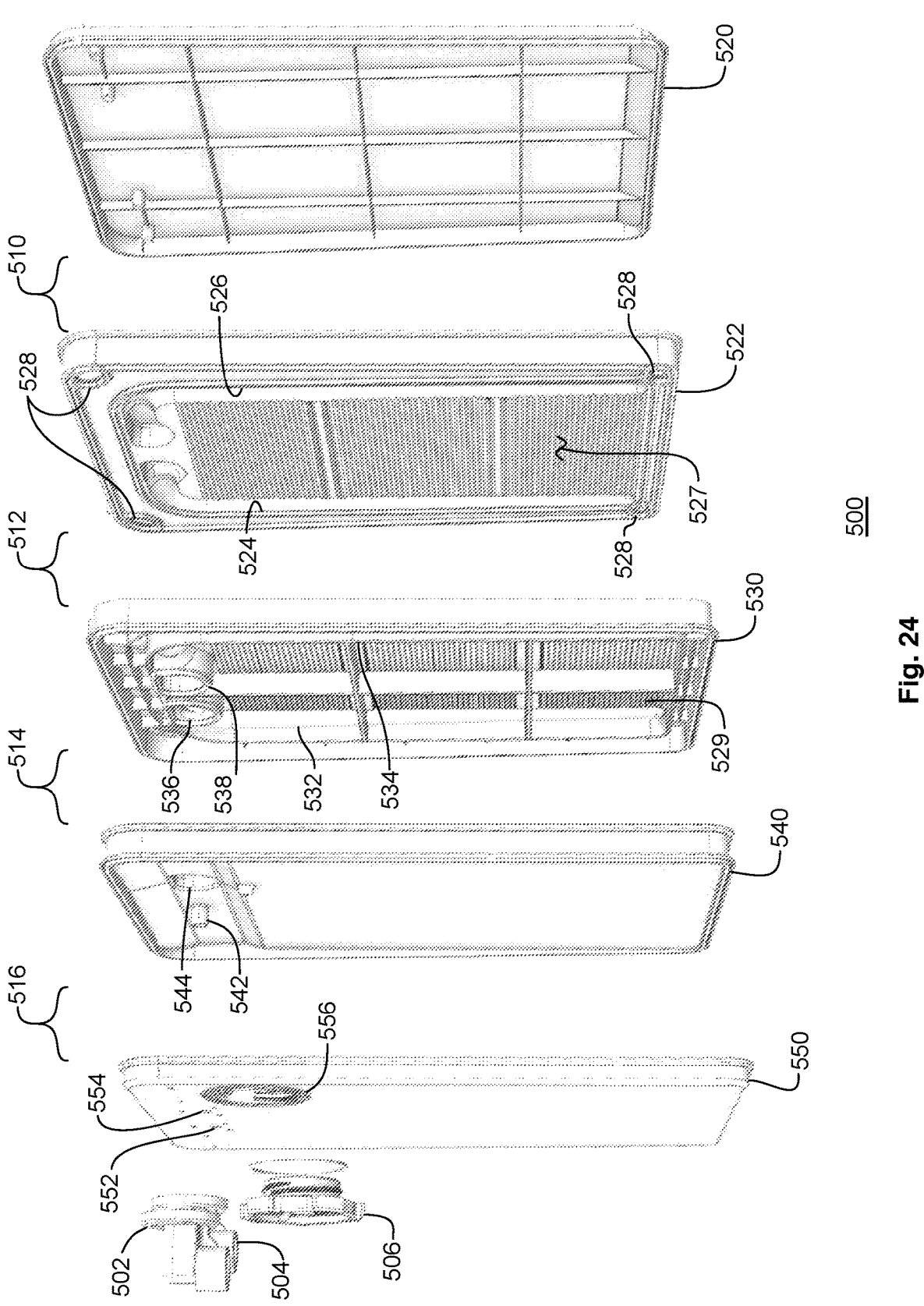
FIG. 24 is an exploded view drawing of coolant heat exchange assembly according to an illustrative embodiment of the present invention.

Reference is directed to FIG. 24, which is an exploded view drawing of coolant heat exchange assembly 500 according to an illustrative embodiment of the present invention. This drawing illustrates the several molded components 520, 522, 530, 540, and 550 that are assembled to form the coolant heat exchange assembly 500 and thereby also define the several internal volumetric compartments including the lower and upper coolant tanks 510, 514, respectively, the heat exchanger 512, and the thermal fluid reservoir volume 516 (identified by open brackets in FIG. 24). Note that in this illustrative embodiment, the molded components are injection molded thermoplastics for low cost, and are joined together using thermal fusion techniques, such as hot plate welding. In the hot plate welding technique, joining surfaces of adjacent molded components are heated to thermal fusion temperatures by a hot plate, which is suddenly removed as the molded components are aligned and urged together, thereby fusing them into a single, strong, and fluid-tight, unit. This process is repeated between all the adjacent molded components 520, 522, 530, 540, and 550.

The heat exchanger in FIG. 24 is formed of molded components 522 and 530 as they are fused together, joining respective portions of the plural heat exchange tubes 527, 529, as well as respective portions of the inlet manifold 526, 533 and the outlet manifold 524, 532. Molded component 530 also provides passageways for thermal fluid inlet 538 and for thermal fluid outlet 536 from the hear exchanger. A bottom molded component 520 is fused to molded component 522, thereby forming the lower coolant tank volume 510. Similarly, molded component 540 is fused to molded component 530, thereby forming the upper coolant tank volume 514. Note that plural passageways 528 are formed through the heat exchanger 522, 530, so that the lower coolant tank area 510 and upper coolant tank area are fluidly coupled together.

Intermediate molded component 540 is used to define both the upper coolant tank volume 514 and the thermal fluid reservoir volume 516 as it is fused with upper molded component 550. Intermediate molded component 540 includes the thermal fluid drain opening 544 and the thermal fluid outlet riser 542. These passageways facilitate movement of the thermal fluid between internal volumes, as defined above. In this disclosure, a fluid riser is a fluid conduit that passes through a given volume without fluid coupling to such volume. For example, the thermal fluid passing through the thermal fluid outlet riser 542 does not mix with the thermal fluids contained in the thermal fluid reservoir volume 516. The upper molded component 550 includes an inlet aperture 554 that enables thermal fluid entering the thermal fluid inlet coupler fitting 502 to flow into the thermal fluid reservoir volume 516. The upper molded component 550 also includes an outlet aperture 552 that enables thermal fluid exiting the thermal fluid outlet riser 542 to pass into the thermal fluid outlet coupler fitting 504. The combination fill cap and vacuum relief valve 506 threadably engages a fill port 556 formed through the upper molded component 550, as illustrated. In another illustrative embodiment, a second fill port and cap (not shown) for the lower coolant tank 510 is added such that it may be filled independently of the upper coolant tank 516.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. A coolant heat exchange assembly that supplies chilled thermal fluid to a control unit having a thermal fluid supply coupler coupled to an inlet of a pump therein, the pump having a discharge coupled to a thermal body wrap through an umbilical tube assembly, wherein the pump circulates thermal fluid to absorb heat and return through the umbilical tube assembly to a thermal fluid return coupler, the coolant heat exchange assembly comprising:

a coolant tank for containing coolant, and having a heat exchanger disposed therein for circulating thermal fluid therethrough, wherein said heat exchanger includes an inlet manifold and an outlet manifold with plural heat exchange tubes disposed therebetween, and further including a thermal fluid outlet riser coupled to said outlet manifold and passing through said coolant tank to a thermal fluid outlet coupler located exterior of said coolant tank, which is selectively connectable to the thermal fluid supply coupler for providing chilled thermal fluid thereto upon operation of the pump;

a thermal fluid reservoir having a thermal fluid inlet coupler that is selectively connectable to the thermal fluid return coupler for receiving thermal fluid therefrom, and having a thermal fluid outlet drain coupled to said inlet manifold for delivering thermal fluid thereto, and having a vacuum relief valve for venting air into said thermal fluid reservoir to prevent formation of a vacuum in the thermal fluid reservoir, and wherein said heat exchanger includes a first heat exchanger molding portion and a second heat exchanger molding portion, which are cooperatively formed to define opposing halves of said plural heat exchange tubes when assembled together in clamshell fashion.

2. The assembly of claim 1, and wherein said first heat exchanger molding portion and said second heat exchanger molding portion are further cooperatively formed to define opposing halves of said inlet manifold and said outlet manifold, which define said inlet manifold and said outlet manifold when assembled together in clamshell fashion.

3. The apparatus of claim 1, and wherein said coolant tank comprises a first coolant tank portion and a second coolant tank portion, which are located on opposing sides of said heat exchanger, and contain a first portion of the coolant and a second portion of the coolant, respectively, and such that said heat exchanger is thermally exposed on opposing sides thereof to both of said first coolant portion and said second coolant portion.

4. The apparatus of claim 3, and wherein:
said first coolant tank portion and said second coolant tank portion each include a separate coolant fill port.

5. The apparatus of claim 1, and wherein:
said thermal fluid outlet coupler is coupled through a thermal fluid outlet riser that passes through said thermal fluid reservoir.

6. The apparatus of claim 1, and wherein:
said coolant is water mixed with an additive to prevent freezing above a temperature of at least minus ten degrees Fahrenheit, and wherein
said thermal fluid is selected from a mixture of water and isopropyl alcohol or propylene glycol, which mixture prevents freezing above a temperature of at least minus ten degrees Fahrenheit.

7. The apparatus of claim 1, and wherein:
said thermal fluid inlet coupler and said thermal fluid outlet coupler are quick-connect tubing couplers having automatic shut-off valves therein to prevent said thermal fluid from leaking when disconnected.

8. The apparatus of claim 1, and wherein:
said coolant heat exchange assembly is fabricated from high density polyethylene (HDPE) plastic.

9. The apparatus of claim 1, and wherein:
said vacuum relief valve is disposed within a thermal fluid fill cap selectively attachable to said thermal fluid reservoir.

10. The apparatus of claim 9, and wherein:
said thermal fluid fill cap includes one or more vent openings;
said vacuum relief valve includes a resilient member that sealably engages said one or more vent openings in said thermal fluid fill cap.

11. The apparatus of claim 1, and wherein:
said coolant tank and said thermal fluid reservoir are formed of layers of molded components that are hot plate welded together, which thereby form said coolant tank and said thermal fluid reservoir.

12. The apparatus of claim 1, and wherein:
said vacuum relief valve is disposed within a wall of the thermal fluid reservoir.

13. A coolant heat exchange assembly that supplies chilled thermal fluid to a control unit having a thermal fluid supply coupler coupled to an inlet of a pump therein, the pump having a discharge coupled to a thermal body wrap through an umbilical tube assembly, wherein the pump circulates thermal fluid to absorb heat and return through the umbilical tube assembly to a thermal fluid return coupler, the coolant heat exchange assembly comprising:
a coolant tank for containing coolant, and having a heat exchanger disposed therein for circulating thermal fluid therethrough, wherein said heat exchanger includes an inlet manifold and an outlet manifold with plural heat exchange tubes disposed therebetween, and further including a thermal fluid outlet riser coupled to said outlet manifold and passing through said coolant tank to a thermal fluid outlet coupler located exterior of said coolant tank, which is selectively connectable to the thermal fluid supply coupler for providing chilled thermal fluid thereto upon operation of the pump;
a thermal fluid reservoir having a thermal fluid inlet coupler that is selectively connectable to the thermal fluid return coupler for receiving thermal fluid therefrom, and having a thermal fluid outlet drain coupled to said inlet manifold for delivering thermal fluid thereto; and wherein
said heat exchanger includes a first heat exchanger molding portion and a second heat exchanger molding portion, which are cooperatively formed to define opposing halves of said plural heat exchange tubes when assembled together in clamshell fashion.

14. The apparatus of claim 13 further comprising a vacuum relief valve disposed to enable entry of an amount of air into a thermal-fluid circulation system comprising said thermal fluid reservoir, said inlet manifold, said heat exchange tubes, said outlet manifold, and said thermal fluid outlet riser.

15. The apparatus of claim 14 wherein the vacuum relief valve is configured to open if the internal pressure of the thermal-fluid circulation system is lower than an atmospheric pressure.

* * * * *